(12) United States Patent
Weissbach et al.

(10) Patent No.: US 8,871,971 B2
(45) Date of Patent: *Oct. 28, 2014

(54) PROTECTION OF NORMAL CELLS

(71) Applicant: CHS Pharma, Inc., Jupiter, FL (US)

(72) Inventors: Herbert Weissbach, Boyton Beach, FL (US); Nathan Brot, Lake Worth, FL (US)

(73) Assignee: CHS Pharma, Inc., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,218

(22) Filed: Jul. 16, 2013

(65) Prior Publication Data
US 2014/0018429 A1 Jan. 16, 2014

Related U.S. Application Data

(60) Continuation of application No. 12/115,331, filed on May 5, 2008, now Pat. No. 8,487,128, which is a continuation-in-part of application No. 11/512,616, filed on Aug. 29, 2006, now Pat. No. 7,414,139, which is a division of application No. 10/723,809, filed on Nov. 26, 2003, now Pat. No. 7,129,374.

(60) Provisional application No. 60/429,269, filed on Nov. 26, 2002.

(51) Int. Cl.
*C07C 315/00* (2006.01)
*A61K 31/192* (2006.01)

(52) U.S. Cl.
CPC .................................. *A61K 31/192* (2013.01)
USPC ........... 562/429; 562/427; 562/428; 514/562; 514/568

(58) Field of Classification Search
None
See application file for complete search history.

(56) References Cited

U.S. PATENT DOCUMENTS 8,487,128 B2 * 7/2013 Weissbach et al. ........... 562/429

* cited by examiner

*Primary Examiner* — Sudhakar Katakam
(74) *Attorney, Agent, or Firm* — Stanley A. Kim

(57) ABSTRACT

The invention provides compositions comprising sulindac, R-epimer sulindac, S-epimer sulindac, derivatives, metabolites, and structural analogs thereof which protect normal cells against damage caused by solar rays, oxidative damage, environmental factors, diseases and organisms.

2 Claims, 19 Drawing Sheets

PROTECTION OF NORMAL CELLS

CROSS REFERENCE TO RELATED APPLICATION

The present application is a continuation application of U.S. patent application Ser. No. 12/115,331, filed May 5, 2008, now U.S. Pat. No. 8,487,128, which is a continuation in part of U.S. patent application Ser. No. 11/512,616 filed Aug. 29, 2006, now U.S. Pat. No. 7,414,139, which is a divisional application of U.S. patent application Ser. No. 10/723,809 filed Nov. 26, 2003, now U.S. Pat. No. 7,129,374, which claims the priority of U.S. provisional application No. 60/429,269 filed on Nov. 26, 2002, which are incorporated herein by reference in their entirety.

FIELD OF THE INVENTION

The invention relates to the fields of biochemistry, pharmacology, and medicine. More particularly, the invention relates to methods and compositions for promoting health and increasing longevity by reducing oxidative damage to cells and tissues.

BACKGROUND

Oxygen is involved in a wide range of normal metabolic reactions and is essential for the survival of all aerobic organisms, including human beings. Reactive oxygen species (ROS), such as superoxide, are produced in abundance as a byproduct of the incomplete reduction of oxygen that has entered the respiratory chain. Superoxide is the precursor of other damaging oxygen species including hydrogen peroxide, the hypochlorite ion and the hydroxyl radical. Oxidase enzymes in cells such as phagocytes and nitric oxide synthases are other sources of ROS.

While low levels of ROS are present under normal physiological conditions, in excess, ROS can cause oxidative damage to cells and tissues by, for example, oxidizing cellular macromolecules such as nucleic acids, lipids and proteins. Cumulative damage to cells in this manner can result in pathology. Not surprisingly then, oxidative damage has been implicated in a wide variety of diseases and conditions including chronic obstructive lung disorders such as smoker's emphysema, reperfusion damage, neurodegenerative diseases such as Alzheimer's disease, Parkinson's disease, and amyotrophic lateral sclerosis (ALS), heart attacks, stroke, several autoimmune diseases, and aging.

Regarding the latter, oxidative damage to cellular macromolecules has been postulated to accelerate the aging process and shorten lifespan. For example, the level of oxidized methionine in proteins in an animal has been observed to increase with the age of the animal. Moreover, in *Drosophila*, greater resistance to ROS via over-expression of superoxide dismutase and catalase has been correlated with longer lifespan, whereas genetic disruption of superoxide dismutase and catalase has been correlated with shorter lifespan.

Although cells have evolved their own enzymatic antioxidant systems (e.g., superoxide dismutase, catalase, and peroxidase) to neutralize ROS, such systems may not function at ideal levels to minimize the rate of aging and the development of disease. Accordingly, there is a clear need for non-naturally occurring compositions and methods that prevent or reduce oxidative damage to cells. One approach to increase the antioxidant activity in cells is to provide cells with compounds that directly scavenge ROS, e.g., vitamins C, E, and A, glutathione, ubiquinone, uric acid, carotenoids, and the like. Such conventional antioxidant compounds, however, lose activity after neutralizing only one or two ROS molecules. They are thus limited by the relatively small quantities of ROS that they can destroy.

SUMMARY

The invention relates to the protection of normal cells against damage by environmental factors, such as ultra violet irradiation, or in vivo and intra cellular factors such as oxidative damage. A composition for the protection of normal cells comprises a sulindac, R-epimers of sulindac, S-epimers of sulindac and mixtures thereof.

In a preferred embodiment, a method of protecting normal cells from damage in a subject, comprises providing a composition comprising sulindac, R-epimer sulindac, S-epimer sulindac, derivatives, metabolites, and structural analogs thereof, said sulindac, R-epimer sulindac, S-epimer sulindac, derivatives, metabolites, and structural analogs thereof having a concentration of at least about 0.010% w/w; contacting at least one living cell with an amount of said sulindac in a therapeutically effective dose; and, protecting normal cells from damage in a subject.

In another preferred embodiment, the sulindac, R-epimer sulindac, S-epimer sulindac, derivatives, metabolites, and structural analogs thereof are in a concentration range of about 0.001% w/w up to 100% w/w.

In another preferred embodiment, the composition comprising sulindac, R-epimer sulindac, S-epimer sulindac, derivatives, metabolites, and structural analogs thereof is administered systemically, intra-peritoneally, intra-venously, sub-cutaneously, intra-muscularly, and topically.

In another preferred embodiment, the composition comprises sulindac, sulindac, derivatives, metabolites, and structural analogs thereof.

In another preferred embodiment, the composition comprises R-epimer sulindac, derivatives, metabolites, and structural analogs thereof.

In another preferred embodiment, the composition comprises S-epimer sulindac, derivatives, metabolites, and structural analogs thereof.

In another preferred embodiment, the composition comprises one or more of sulindac, R-epimer sulindac, S-epimer sulindac, derivatives, metabolites, and structural analogs thereof.

In another preferred embodiment, the composition comprises varying ratios of sulindac, R-epimer sulindac, S-epimer sulindac, derivatives, metabolites, and structural analogs thereof.

In another preferred embodiment, the ratio of sulindac:R-epimer sulindac:S-epimer sulindac is from about 0 to 1000.

In another preferred embodiment, the composition protects normal cells from damage comprising environmental damage, disease conditions, organisms, or solar rays.

In another preferred embodiment, the composition protects normal cells from oxidative damage.

Definitions

In accordance with the present invention and as used herein, the following terms are defined with the following meanings, unless explicitly stated otherwise.

As used herein, "a", "an," and "the" include plural references unless the context clearly dictates otherwise.

As used herein, the terms "methionine moiety" and "methionine analog" include all structures encompassed by general methionine formula 1 described herein, including selenomethionine derivatives.

As used herein, the term "catalytic antioxidant" refers to a non-naturally occurring (or purified, naturally occurring) antioxidant compound that can be enzymatically regenerated after it is oxidized by an oxidizing agent (for example a ROS) such that each equivalent of antioxidant compound can destroy more than one equivalent of the oxidizing agent.

As used herein, "protecting" or "protection" of normal cells refers to any damage a cell can sustain, in particular, oxidative damage from environmental factors, for example, the sun, carcinogens; diseases, such as neurological diseases, cancer, drugs such as adriamycin and arsenic trioxide, diseases caused by organisms, such as viruses, bacteria and the like. In one embodiment, "damage" refers to oxidative damage. Protecting against oxidative damage comprises preventing, inhibiting, reducing reactive oxidation intermediates which cause damage to a cell.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma. The terms "tumor" and "tumor cell" as used herein refer to a cell or aggregation of cells characterized by or resulting from uncontrolled, progressive growth and division of cells. Such cells generally have a deleterious effect on a host organism. A tumor cell may be located in vivo, particularly in a human but also including other animals. A tumor cell may also be located in vitro, and may be treated according to inventive methods and using inventive compositions, for instance for research and/or drug discovery. Inhibition of a tumor cell includes inhibition of growth of such a cell, inhibition of physiological processes, inhibition of metastasis, and preferably includes killing such a cell.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" "subject" or "individual" are used interchangeably herein, and refers to a mammalian, animal, avian or reptilian subject to be protected from damage to normal cells, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

A "micro sphere" or "micro particle", as defined herein, includes a particle of a biocompatible solid-phase material having a diameter of about one millimeter to about one micrometer, or less, wherein the particle may contain a biologically active agent and, wherein the solid-phase material sustains the release of the composition comprising an effective amount of sulindac, R-epimer of sulindac, S-epimer of sulindac, derivatives, variants, structural analogs and mixtures thereof, from the micro sphere. A micro sphere can have a spherical, non-spherical or irregular shape. The typical micro sphere shape is generally spherical.

A "biocompatible" material, as defined herein, means that the material, and any degradation products of the material, is non-toxic to the recipient and also presents no significant deleterious or untoward effects on the recipient's body.

The term "sustained release" (i.e., extended release and/or controlled release) are used herein to refer to a composition comprising an effective amount of sulindac, R-epimer of sulindac, S-epimer of sulindac, derivatives, variants, structural analogs and mixtures thereof that is administered to a subject and that continuously releases a stream of one or more sulindac components (e.g. sulindac, R-epimer of sulindac, S-epimer of sulindac, derivatives, variants, structural analogs and mixtures thereof) over a predetermined time period and at a level sufficient to achieve a desired effect (e.g. protecting cells or whole animal from solar rays) throughout the predetermined time period. Reference to a continuous release stream is intended to encompass release that occurs as the result of biodegradation of the composition, or a matrix or component thereof, or as the result of metabolic transformation or dissolution of the added nutrients or other desired agent(s).

Unless otherwise defined, all technical terms used herein have the same meaning as commonly understood by one of ordinary skill in the art to which this invention belongs.

Although methods and materials similar or equivalent to those described herein can be used in the practice or testing of the present invention, suitable methods and materials are described below. The particular embodiments discussed below are illustrative only and not intended to be limiting. All publications, patent applications, patents, and other references mentioned herein are incorporated by reference in their entirety. In the case of conflict, the present specification, including definitions will control.

DETAILED DESCRIPTION

The invention encompasses compositions and methods relating to protection of normal cells by a variety of factors resulting in oxidative damage, such as exposure to the sun, for example ultraviolet radiation; damage caused by in vivo factors, such as, for example, oxidative damage caused by any number of diseases.

The below described preferred embodiments illustrate various compositions and methods within the invention. Nonetheless, from the description of these embodiments, other aspects of the invention can be made and/or practiced based on the description provided below.

Biological Methods

Methods involving conventional chemistry, cell biology and molecular biology techniques are described herein. Such techniques are generally known in the art and are described in detail in methodology treatises such as Classics in Total Synthesis. Targets, Strategies, Methods, K. C. Nicolaou and E. J. Sorensen, VCH, New York, 1996; and The Logic of Chemical Synthesis, E. J. Coney and Xue-Min Cheng, Wiley & Sons, NY, 1989. Molecular biological and cell biological methods are described in treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Catalytic Antioxidants

The invention provides small molecules containing at least one (e.g., 1, 2, 3 or more) methyl sulfoxide or methyl sulfide group that can enter cells and prevent oxidative damage by a catalytic antioxidant mechanism. The methyl sulfide group on the compounds reacts with ROS, forming methyl sulfoxide. The methyl sulfoxide-bearing compounds, in turn, act as substrates for Msr enzymes, and/or other enzymes, which reduce the compounds and thereby regenerate their antioxidant properties. These compounds can be administered to cells or animals to reduce cellular damage caused by ROS.

Figure 1:
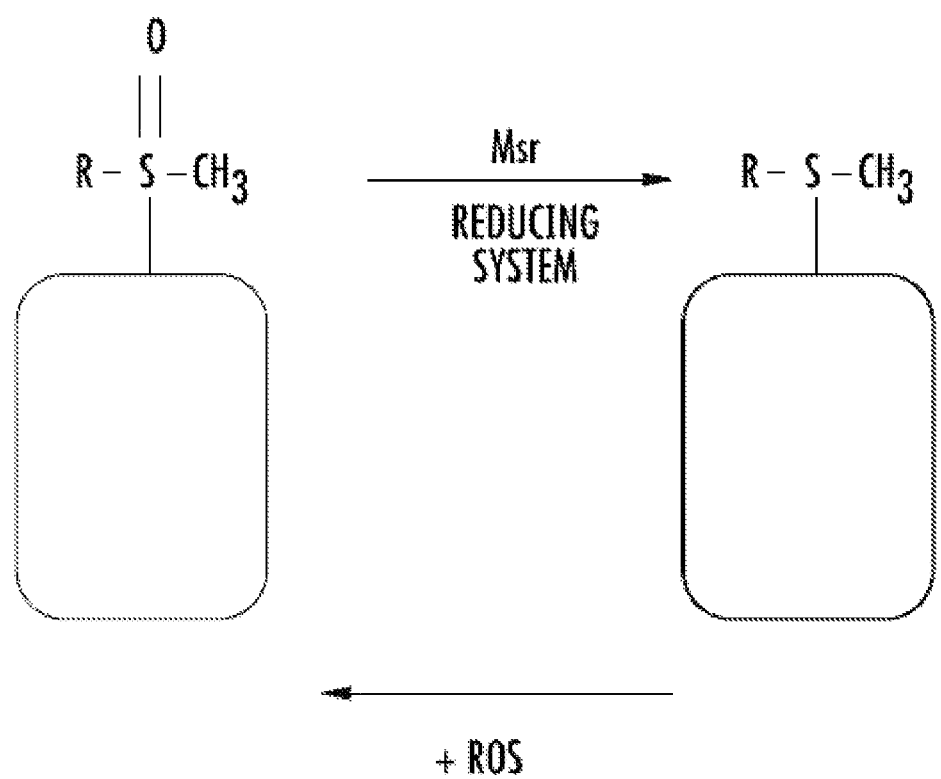
FIG. 1 is a schematic diagram showing the mechanism of action of a catalytic antioxidant, according to an embodiment of the invention.

Referring to FIG. 1, these compounds serve 1) as ROS scavengers (antioxidants) by virtue of the active groups within their structures that destroy or react with ROS, and 2) as catalytic antioxidants that reduce the oxidized compounds back to the unoxidized form capable of further reaction with ROS. The catalytic nature of the antioxidant compounds of the invention is due to their ability to serve as substrates for Msr enzymes and/or any other enzyme that can reduce the sulfoxide moiety to the sulfide. The core functional group recognized by these enzymes is methyl sulfoxide. In the case of N-methionine-containing peptide and protein substrates, this functional group is contained within the amino acid methionine.

Figure 2:
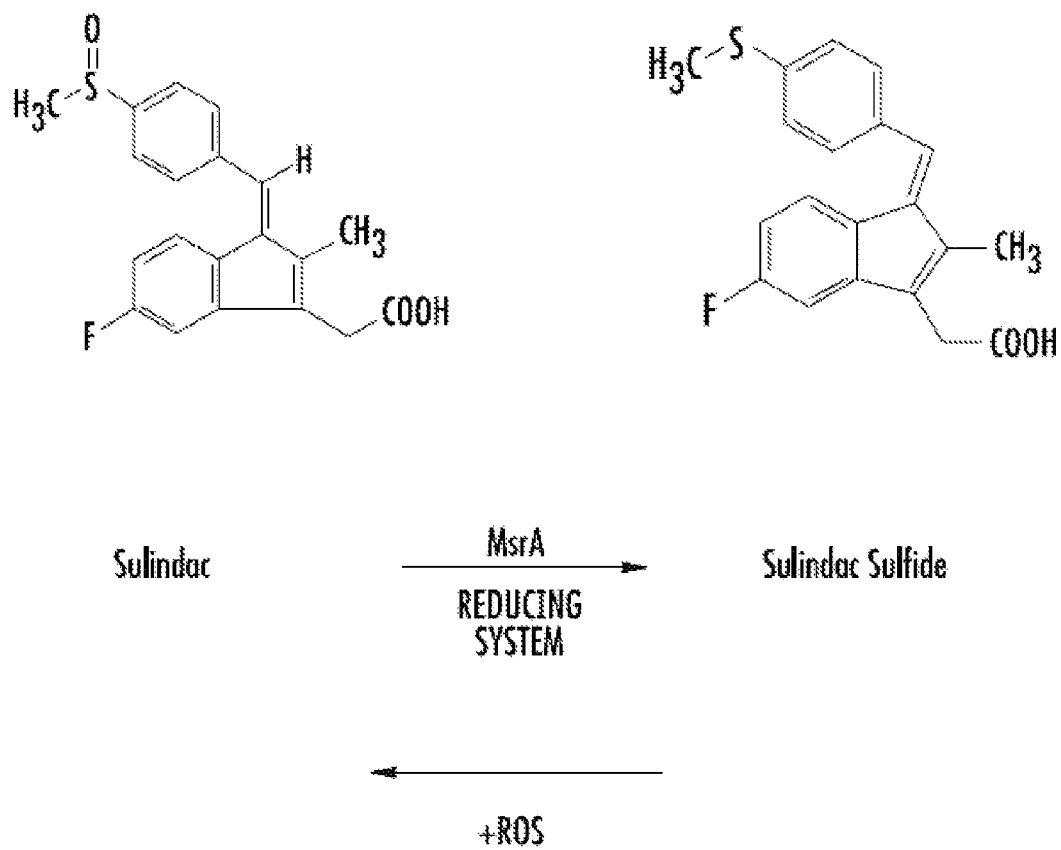
FIG. 2 is a schematic diagram showing the cycle of catalytic antioxidant activity of sulindac, catalyzed by an MsrA enzyme, according to an embodiment of the invention.

Any compound having a methyl sulfide or methyl sulfoxide functional group that can be a substrate for an Msr enzyme and/or any other enzyme that can reduce the sulfoxide moiety to the sulfide can be used. Sulindac, a non-steroidal anti-inflammatory drug and COX inhibitor, is one example of a methyl sulfoxide-containing compound that serves as a substrate for Msr enzymes. Sulindac is a pro drug, and is only active as a COX inhibitor when the methyl sulfoxide moiety on the molecule is reduced to the sulfide. Heretofore, sulindac was not known to act as a substrate for a Msr. FIG. 2 shows the reduction of sulindac to sulindac sulfide, catalyzed by Msr. As described below, sulindac was tested as a substrate against six known members of the Msr family identified in bacteria (*E. coli*) and against Msr enzymes present in mammalian (bovine) tissues. MsrA and a membrane-associated Msr of bacteria were shown to be able to reduce sulindac to the active sulfide. In mammalian tissues, reduction of sulindac was primarily attributable to the activity of MsrA.

As further described below, sulindac administration (1) protected *Drosophila* against the damage from paraquat-induced ROS production, (2) prolonged the survival of spinal cord motor neurons in mice with a neurodegenerative disease caused by oxidative damage, and (3) extended the lifespan of the foregoing mice.

Methionine-Based Catalytic Antioxidants

In one aspect, the invention provides catalytic antioxidant compounds having methionine moieties or analogs of methionine. Such compounds can be a substrate for Msr enzymes that recognize the methyl sulfoxide functional group in methionine (for example, MsrA and MsrB) and/or any other enzyme that can reduce the sulfoxide moiety to the sulfide. The methionine moiety or analog found in the methionine-containing embodiments of the compounds has the following general structure:

general methionine formula (1)

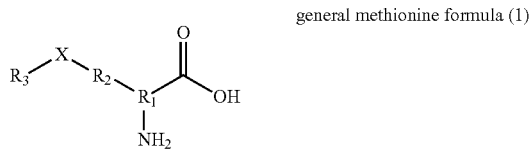

Groups $R_1$, $R_2$, $R_3$, and X in general structure 1 are defined as follows:

$R_1$ may be CH (of either D or L configuration).

$R_2$ may be a normal or branched alkyl or fluoroalkyl group having 1 to 6 carbons.

$R_3$ may be ethyl or preferably methyl, or a fluorinated derivative thereof.

X may be either S or Se in any oxidation state.

As used herein, the terms "methionine moiety" and "methionine analog" include all structures encompassed by general formula 1, including selenomethionine analogs of methionine.

General structure 1 also includes esters and salts of the carboxylic acid. Oligopeptides containing methionine for attachment to small molecules are also encompassed by the invention.

Methionine-Based Catalytic Antioxidants Derived from COX Inhibitors

Inflammation and oxidative damage are known to coexist in many disease states and degenerative conditions. Accordingly, particularly preferred embodiments of the methionine-containing compounds of the invention are derivatives of anti-inflammatory agents such as COX inhibitors. Non-limiting examples of such compounds, employing scaffolds based on several COX inhibitors, and methods for their synthesis are provided in the examples below. Exemplary compounds include those derived from the following scaffolds: sulindac, both R- and S-epimers of sulindac; acetyl salicylic acid (ortho-acetoxybenzoic acid), mefenamic acid (2-[(2,3-Dimethylphenyl)amino]benzoic acid); ibuprofen (α-methyl-4-(2-methylpropyl)-benzeneacetic acid); indomethacin (1-(p-chlorobenzoyl)-5-methoxy-2-methyl-indole-3-acetic acid); and rofecoxib (4-[4-(methylsulfonyl)phenyl]-3-phenyl-2(5H)-furanone, for example, Vioxx®, sold by Merck) and celecoxib (4-[5-(4-methylphenyl)-3-(trifluoromethyl)-1H-pyrazol-1-yl]-benzenesulfonamide, for example, Celebrex® sold by Pfizer.

Embodiments of the invention that are sulindac derivatives can have the following general formulas 2-5:

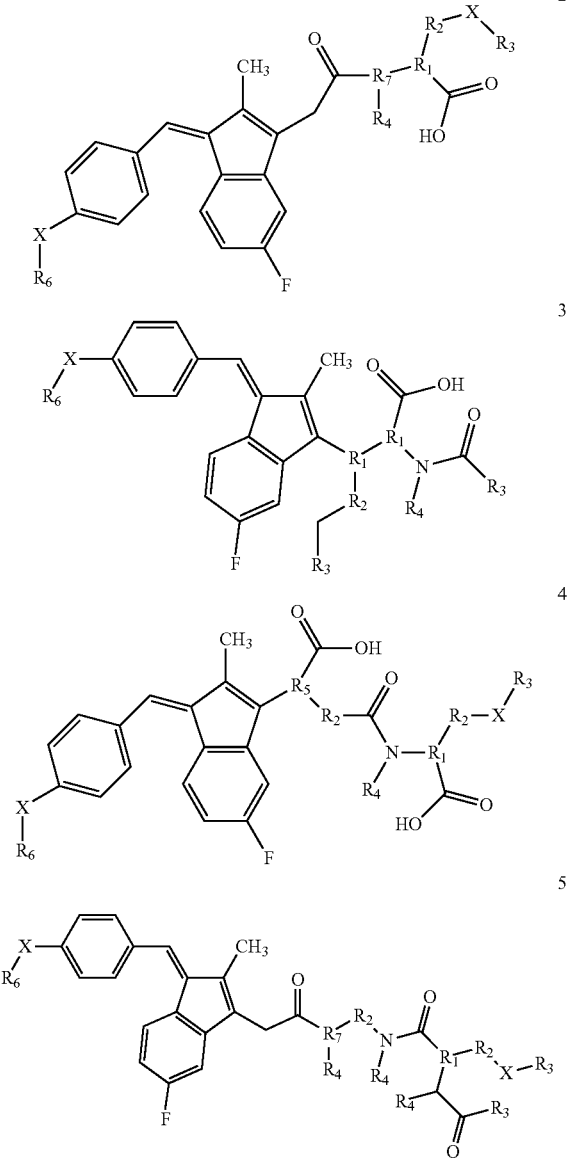

Groups $R_1$, $R_2$, $R_3$, $R_4$, $R_5$, $R_6$, and X in general formulas 2, 3, 4 and 5 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl, or a fluorinated derivative thereof.

$R_4$ may be a hydrogen or a normal or branched alkyl group having 1 to 6 carbons.

$R_5$ may be a CH (of either R or S configuration).

$R_6$ may be a hydrogen or a normal or branched alkyl or fluoroalkyl group having 1 to 6 carbons.

$R_7$ is a nitrogen.

X may be either S or Se in any oxidation state.

General structures 2, 3, 4 and 5 also include esters and salts of the carboxylic acid group. The invention also encompasses sulindac derivatives containing oligomeric methionine moieties and analogs.

Embodiments of the invention that are acetyl salicylic acid derivatives can have the following general formula:

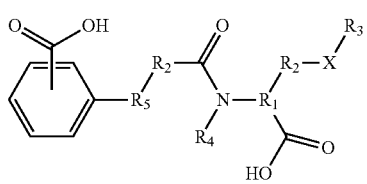

6

The aromatic ring of general structure 6 may contain one or more nitrogen atoms (for example pyridine or pyrazine). The aromatic carboxyl group in general structure 6 may be oriented ortho, meta, or para to the methionine-based moiety. Groups $R_1$, $R_2$, $R_3$, $R_4$, $R_5$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

$R_5$ may be an oxygen.

X may be either S or Se in any oxidation state.

General structure 6 also includes esters and salts of the carboxylic acid group. The invention also encompasses acetyl salicylic acid derivatives containing oligomeric methionine moieties and analogs.

Embodiments of the invention that are mefenamic acid derivatives can have the following general formula:

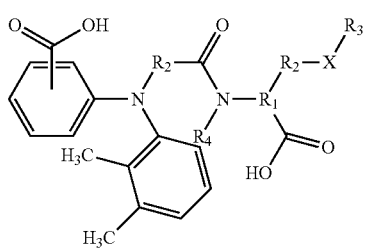

7

Both aromatic rings of general structure 7 may contain one or more nitrogen atoms (for example pyridine or pyrazine). The aromatic carboxyl group in general structure 7 may be oriented ortho, meta, or para to the aniline nitrogen. Groups $R_1$, $R_2$, $R_3$, $R_4$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

X may be either S or Se in any oxidation state.

General structure 7 also includes esters and salts of the carboxylic acid group. The invention also encompasses mefenamic acid derivatives containing oligomeric methionine moieties and analogs.

Embodiments of the invention that are ibuprofen derivatives can have the following general formula:

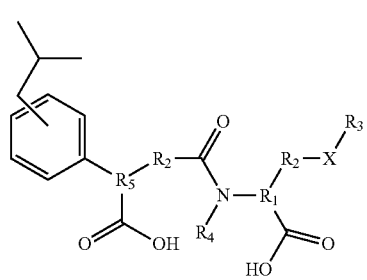

8

The aromatic ring of general structure 8 may contain one or more nitrogen atoms (for example pyridine or pyrazine). The sec-butyl group in general structure 8 may be oriented ortho, meta, or para to the methionine-based moiety. Groups $R_1$, $R_2$, $R_3$, $R_4$, $R_5$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

$R_5$ may be a CH (of either R or S configuration).

X may be either S or Se in any oxidation state.

General structure 8 also includes esters and salts of the carboxylic acid group. The invention also encompasses ibuprofen derivatives containing oligomeric methionine moieties and analogs.

Embodiments of the invention that are indomethacin derivatives can have the following general formula:

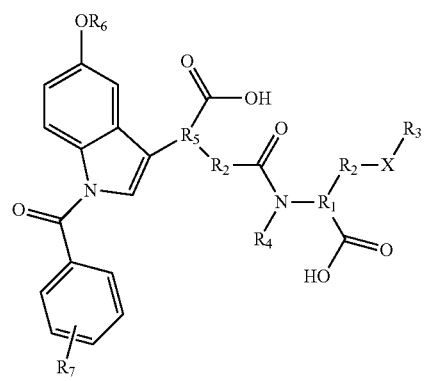

9

Groups $R_1$, $R_2$, $R_3$, $R_4$, $R_5$, $R_6$, $R_7$ and X in general structure 9 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

$R_5$ may be a CH (of either R or S configuration).

$R_6$ is a may be a hydrogen or a normal or branched alkyl or fluoroalkyl group consisting of 1 to 6 carbons.

$R_7$ may be any halogen oriented ortho, meta, or para to the carbonyl group.

X may be either S or Se in any oxidation state.

General structure 9 also includes esters and salts of the carboxylic acid group. The invention also encompasses indomethacin derivatives containing oligomeric methionine moieties and analogs.

Embodiments of the invention that are Vioxx® derivatives can have the following general formula:

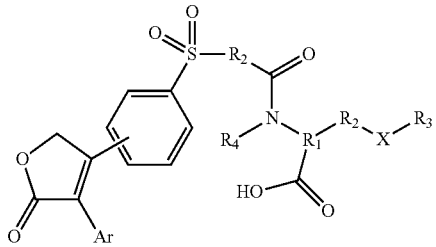

The lactone ring in general structure 10 may be oriented ortho, meta, or para to sulfonyl group. Groups $R_1$, $R_2$, $R_3$, $R_4$, and X in general structure 10 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

X may be either S or Se in any oxidation state.

Ar may be phenyl, alkyl and halogen substituted phenyl, and heteroaromatic compounds.

General structure 10 also includes esters and salts of the carboxylic acid group. The invention also encompasses Vioxx® derivatives containing oligomeric methionine moieties and analogs.

Protecting Normal Cells

In a preferred embodiment, a method of protecting normal cells, both in vivo and in vitro in a subject, from damage comprises administering to an animal, a composition comprising an effective amount of sulindac, R-epimer of sulindac, S-epimer of sulindac, derivatives, variants, structural analogs and mixtures thereof.

In another preferred embodiment, the composition comprises a therapeutically effective concentration of R-epimers of sulindac, structural analogs or derivatives thereof.

In another preferred embodiment, the composition comprises a therapeutically effective concentration of S-epimers of sulindac, structural analogs or derivatives thereof.

In another preferred embodiment, the composition comprises a therapeutically effective concentration of sulindac, structural analogs or derivatives thereof.

In another preferred embodiment, the sulindac comprises R- and S-epimers of sulindac. Preferably, the sulindac is an R-epimer. We have found that in normal cells, in culture but not cancer cells, the R-epimer of sulindac is not efficiently converted to the sulfide, the active COX inhibitor. Since COX inhibitors produce serious toxicity, it is expected that the R-epimer of sulindac can be a potentially superior therapeutic agent because it would have a lower toxicity profile in normal cells. We have also discovered that sulindac, R- and S-epimers of sulindac, in particular the R-epimer of sulindac protects normal cells against damage, for example, oxidative damage.

Figure 14:
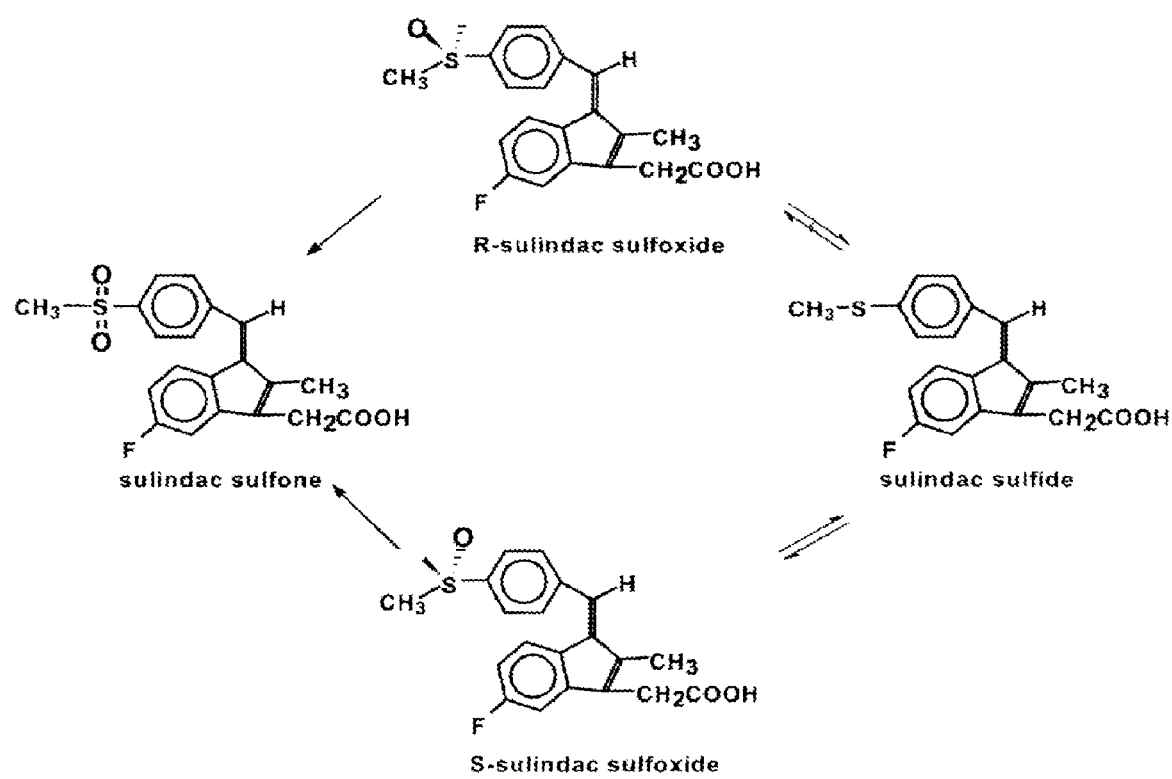
FIG. 14 is a schematic representation showing the structure of sulindac and its metabolites. Sulindac refers to a mixture of R- and S-epimers of sulindac sulfoxide. Theoretically, both the R-sulindac sulfoxide and S-sulindac sulfoxide can be oxidized to form sulindac sulfone or reduced to form sulindac sulfide.

Sulindac, unlike its metabolites, is a chiral compound since it contains a methyl sulfoxide moiety, in which there is asymmetry around the sulfur atom (FIG. 14). Reduction of either epimer of sulindac, which is a prodrug, will yield sulindac sulfide, which is the active COX inhibitor. The R-epimer of sulindac would be advantageous to other compounds as if it would not be less efficiently converted to a COX inhibitor in normal cells in vivo.

In another preferred embodiment, the composition comprises an R-epimer and/or S-epimer of sulindac, derivatives and structural analogs thereof, said R-epimer sulindac, derivatives and variants thereof, having a concentration of at least about 10% w/w; contacting at least one living cell with an amount of said sulindac in a therapeutically effective dose; and, protecting the normal cell from damage. For example, in a lotion, ointment, liquid etc, to be used as a sun screen by a subject to protect cells from solar rays, a composition comprising an effective amount of sulindac, R-epimer of sulindac, S-epimer of sulindac, derivatives, variants, structural analogs and mixtures thereof, provides protection (e.g. oxidative damage) of cells as measured by, for example, generation of oxygen radicals. Measurements of oxidative stress, radicals and the like are known to one of ordinary skill in the art. Other measurements for damage and protection of normal cells against damage include, for example, measurement of biomarkers, heat shock proteins or genes encoding heat shock proteins, biomarkers of hypoxia, such as, for example, in heart cells.

In some embodiments, a biomarker for heat shock proteins can be, for example, a gene, mutants, variants or fragments thereof, encoding heat shock protein (Hsp105), chaperonin subunit 5 (epsilon) (Cct5), chaperonin subunit 8 (theta) (Cct8), DnaJ (Hsp40) homolog, subfamily A, member 1 (Dnaja1), DnaJ (Hsp40) homolog, subfamily C, member 2 (Dnajc2), DnaJ (Hsp40) homolog, subfamily C, member 7 (Dnajc7), heat shock 70 kD protein 5 (glucose-regulated protein) (Hspa5), heat shock protein (Hsp105), heat shock protein 1, alpha (Hspca), heat shock protein 1, beta (Hspcb), heat shock protein 1A (Hspa1a), heat shock protein 1B (Hspa1b), heat shock protein 4 (Hspa4), heat shock protein 4 (Hspa4), heat shock protein 8 (Hspa8), osmotic stress protein (Osp94), protein disulfide isomerase-related protein (P5-pending), or stress-induced phosphoprotein 1 (Stip1).

Any number of genes, nucleic acid fragments of genes, variants mutants and encoded products thereof, have been indentified as being indicative of cell damage. Examples of such biomarkers include, in some embodiments, a cytochrome P450 family gene comprising, P450, family 2, subfamily b, polypeptide 10 (Cyp2b10), P450, family 2, subfamily c, polypeptide 70 (Cyp2c70), P450, family 2, subfamily c, polypeptide 37 (Cyp2c37), P450, family 2, subfamily a, polypeptide 12 (Cyp2a12), P450, family 2, subfamily c, polypeptide 40 (Cyp2c40), P450, family 3, subfamily a, polypeptide 11 (Cyp3a11), P450, family 3, subfamily a, polypeptide 13 (Cyp3a15), P450, family 3, subfamily a, polypeptide 16 (Cyp3a16), P450, family 3, subfamily a, polypeptide 25 (Cyp3a25), P450, family 2, subfamily a, polypeptide 4 (Cyp2a4), or P450, family 4, subfamily a, polypeptide 10 (Cyp4a10).

In some embodiments, a gene, mutants, variants or fragments thereof, encoding one or more products indicative of DNA damage can be, for example, a nucleic acid sequence encoding ataxia telangiectasia mutated homolog (human) (Atm), damage specific DNA binding protein 1 (Ddb1), excision repair cross-complementing rodent repair deficiency, complementation group 3 (Ercc3), huntingtin-associated protein 1 (Hap1), mutS homolog 2 (*E. coli*) (Msh2), myeloid ecotropic viral integration site-related gene 1 (Mrg1), neuroblastoma ras oncogene (Nras), RAD21 (S. pombe) (Rad21), retinoblastoma 1 (Rb1), retinoblastoma binding protein 4 (Rbbp4), retinoblastoma binding protein 7 (Rbbp7), retinoblastoma binding protein 9 (Rbbp9), spinocerebellar ataxia 2 homolog (human) (Sca2), X-linked myotubular myopathy gene 1 (Mtm1), or X-ray repair complementing defective repair in Chinese hamster cells 5 (Xrcc5).

In some embodiments, a gene, mutants, variants or fragments thereof, encoding one or more products that regulate cell cycle can be, for example, cyclin G1 (Ccng1), cyclin D2 (Ccnd2), CDC23 (cell division cycle 23, yeast, homolog) (Cdc23), cyclin D3 (Ccnd3), cyclin-dependent kinase 5 (Cdk5), p21 (CDKN1A)-activated kinase 2 (Pak2), RAS p21 protein activator 1 (Rasa1), cyclin-dependent kinase 8 (Cdk8), CDC42 effector protein (Rho GTPase binding) 4 (Cdc42ep4), caspase 8 (Casp8), caspase 4, apoptosis-related cysteine protease (Casp4), caspase 12 (Casp12), Bcl-associated death promoter (Bad), Bcl2-like 2 (Bcl2l2), programmed cell death 6 interacting protein (Pdcd6Ip), programmed cell death 8 (Pdcd8), programmed cell death 2 (Pdcd2), annexin A1 (Anxa1), annexin A2 (Anxa2), or signal-induced proliferation associated gene 1 (Sipa1), protein kinase C and Jun kinases.

Any number of the genes, variants, fragments and encoded products thereof can be compared to normal cell profiles in order to further identify cell damage or lack thereof.

In a preferred embodiment, a composition comprises at least about 10% (w/w) R-epimer of sulindac; preferably the composition comprises about 50% (v/v) R-epimer of sulindac; more preferably the composition comprises about 75% (w/w) R-epimer of sulindac; more preferably, the composition comprises about 90% (w/w) R-epimer of sulindac; more preferably, the composition comprises about 95%, 96%, 97%, 98%, 99%, 99.9% (w/w) R-epimer of sulindac.

In another preferred embodiment, sulindac, R- and/or S-epimers, structural analogs or derivatives thereof, are in a concentration of about 1% up to 99.999% w/w.

In another preferred embodiment, the composition comprising R- and/or S-epimers of sulindac, sulindac, derivatives and structural analogs thereof, is administered systemically, intra-peritoneally, intra-venously, sub-cutaneously, intra-muscularly, and topically.

In a preferred embodiment, the composition comprises R- and/or S-epimers of sulindac, sulindac, derivatives and structural analogs thereof, in a sun screen (sun tan lotion) lotion.

In another preferred embodiment, the composition comprises R- and/or S-epimers of sulindac, sulindac, derivatives and structural analogs thereof, in a lotion that is applied topically. For example, in cosmetics, such as lipsticks, face creams or liquids, eye creams or liquids, or any other cosmetic uses. The composition can be a lotion, cream, liquid, a composition comprising R- and/or S-epimers of sulindac, sulindac, derivatives and structural analogs thereof in lipids which can be released in controlled dosages over time, thus providing extended protection. These compositions may be mixed with any one or more compounds such as vitamins, ROI scavengers, cytokines, antibiotics, anti-pyretics and the like.

In a preferred embodiment, these compositions are administered for various indications, including, but not limited to: (1) preventing ischemic/reoxygenation injury in a patient, (2) preserving organs for transplant in an anoxic, hypoxic, or hyperoxic state prior to transplant, (3) protecting normal normal tissues from free radical-induced damage consequent to exposure to ionizing radiation and/or chemotherapy, as with bleomycin, (4) protecting cells and tissues from free radical-induced injury consequent to exposure to xenobiotic compounds which form free radicals, either directly or as a consequence of monooxygenation through the cytochrome P-450 system, (5) enhancing cryopreservation of cells, tissues, organs, and organisms by increasing viability of recovered specimens, and (6) prophylactic administration to prevent: carcinogenesis, cellular senescence, cataract formation, formation of malondialdehyde adducts, HIV pathology and macromolecular crosslinking, such as collagen crosslinking.

In another preferred embodiment, the normal cells are protected by damage caused by environmental factors. Environmental factors include, but not limited to rays from the sun, such as for example, ultra violet rays, gamma rays; carcinogens, heterocyclic amines formed when meats and eggs are cooked at high heat or grilled, such as for example, 2-Amino-3,4-dimethylimidazo[4,5-f]quinoline, 2-Amino-3,8-dimethylimidazo[4,5-f]quinoxaline, 2-Amino-1-methyl-6-phenylimidazo[4,5-b]pyridine; tobacco smoke and the like.

In another preferred embodiment, the normal cells in a subject are protected from damage by organisms such as viruses, bacteria, protozoa, fungi, prions. Examples of viruses causing damage to cells include Human Papillomaviruses viruses, Hepatitis viruses and the like.

In another preferred embodiment, normal cells in a subject are protected from damage caused by diseases, such as for example, neurological diseases, such as Parkinson's disease.

In another preferred embodiment, a composition comprising an effective amount of sulindac, R-epimer of sulindac, S-epimer of sulindac, derivatives, variants, structural analogs and mixtures thereof, are used for preventing oxidative damage in human transplant organs and for inhibiting reoxygenation injury following reperfusion of ischemic tissues.

In general, the composition comprising sulindac, R- and/or S-epimers of sulindac, derivatives, variants and mixtures thereof protect normal cells against oxidative damage. Oxidation of DNA, proteins, and lipids by reactive oxygen species and other radical and non-radical species has been implicated in a host of human diseases. Radicals may be the primary cause for the following conditions, may make the body more susceptible to other disease-initiating factors, may inhibit endogenous defenses and repair processes, and/or may enhance the progression of incipient disease(s). The administration of sulindac, R- and/or S-epimers, structural analogs or derivatives thereof, by one skilled in the art— including consideration of the pharmacokinetics and pharmacodynamics of therapeutic drug delivery protects a subject form damage of normal cells and may inhibit and/or ameliorate said disease conditions. These examples are not to be seen as limiting, and additional disease conditions for which sulindac, R- and/or S-epimers, structural analogs or derivatives thereof, will be obvious to those skilled in the art. Head, Eyes, Ears, Nose, and Throat: age-related macular degeneration (ARMD), retinal detachment, hypertensive retinal disease, uveitis, choroiditis, vitreitis, ocular hemorrhage, degenerative retinal damage, cataractogenesis and cataracts, retinopathy of prematurity, Meuniere's disease, drug-induced ototoxicity (including aminoglycoside and furosemide toxicity), infectious and idiopathic otitis, otitis media, infectious and allergic sinusitis, head and neck cancer; Central Nervous System (brain and spinal cord): senile dementia (including Alzheimer's dementia), Neuman-Pick's disease, neurotoxin reactions, hyperbaric oxygen effects, Parkinson's disease, cerebral and spinal cord trauma, hypertensive cerebrovascular injury, stroke (thromboembolic, thrombotic, and hemorrhagic), infectious encephalitis and meningitis, allergic encephalomyelitis and other demyelinating diseases, amyotrophic lateral sclerosis (ALS), diabetic neuropathy, multiple sclerosis, neuronal ceroid lipofuscinoses, ataxia-telangiectasia syndrome, aluminum, iron, and other heavy metal(s) overload, primary brain carcinoma/malignancy and brain metastases; Cardiovascular: arteriosclerosis, atherosclerosis, peripheral vascular disease, myocardial infarction, chronic stable angina, unstable angina, idiopathic surgical injury (during CABG, PTCA), inflammatory heart disease [as measured and influenced by C-reactive protein (CRP) and myeloperoxidase (MPO)], vascular restenosis, low-density lipoprotein oxidation (ox-LDL), cardiomyopathies, cardiac arrhythmia (ischemic and post-myocardial infarction induced), congestive heart failure (CHF), drug toxicity (including adriamycin and doxorubicin), Keshan disease (selenium deficiency), trypanosomiasis, alcohol cardiomyopathy, venous stasis and injury (including deep venous thrombosis or DVT), thrombophlebitis; Pulmonary: asthma, reactive airways disease, chronic obstructive pulmonary disease (COPD or emphysema), hyperoxia, hyperbaric oxygen effects, cigarette smoke inhalation effects, environmental oxidant pollutant effects, acute respiratory distress syndrome (ARDS), bronchopulmonary dysplasia, mineral dust pneumoconiosis, adriamycin toxicity, bleomycin toxicity, paraquat and other pesticide toxicities, chemical pneumonitis, idiopathic pulmonary interstitial fibrosis, infectious pneumonia (including fungal), sarcoidosis, asbestosis, lung cancer (small- and large-cell), anthrax infection, anthrax toxin exposure; Renal: hypertensive renal disease, end-stage renal disease, diabetic renal disease, infectious glomerulonephritis, nephrotic syndrome, allergic glomerulonephritis, type I-IV hypersensitivity reactions, renal allograft rejection, nephritic antiglomerular basement membrane disease, heavy metal nephrotoxicity, drug-induced (including aminoglycoside, furosemide, and non-steroidal anti-inflammatory) nephrotoxicity, rhabdomyolisis, renal carcinoma; Hepatic: carbon tetrachloride liver injury, endotoxin and lipopolysaccharide liver injury, chronic viral infection (including Hepatitis infection), infectious hepatitis (non-viral etiology), hemachromatosis, Wilson's disease, acetaminophen overdose, congestive heart failure with hepatic congestion, cirrhosis (including alcoholic, viral, and idiopathic etiologies), hepatocellular carcinoma, hepatic metastases; Gastrointestinal: inflammatory bowel disease (including Crohn's disease, ulcerative colitis, and irritable bowel syndrome), colon carcinoma, polyposis, infectious diverticulitis, toxic megacolon, gastritis (including *Helicobacter pylori* infection), gastric carcinoma, esophagitis (including Barrett's esophagus), gastro-esophageal reflux disease (GERD), Whipple's disease, gallstone disease, pancreatitis, abetalipoproteinemia, infectious gastroenteritis, dysentery, nonsteroidal anti-inflammatory drug-induced toxicity; Hematopoietic/Hematologic: Pb (lead) poisoning, drug-induced bone marrow suppression, protoporphyrin photo-oxidation, lymphoma, leukemia, porphyria(s), parasitic infection (including malaria), sickle cell anemia, thalasemia, favism, pernicious anemia, Fanconi's anemia, post-infectious anemia, idiopathic thrombocytopenic purpura (ITP), autoimmune deficiency syndrome (AIDS); Genitourinary: infectious prostatitis, prostate carcinoma, benign prostatic hypertrophy (BPH), urethritis, orchitis, testicular torsion, cervicitis, cervical carcinoma, ovarian carcinoma, uterine carcinoma, vaginitis, vaginismus; Musculoskeletal: osteoarthritis, rheumatoid arthritis, tendonitis, muscular dystrophy, degenerative disc disease, degenerative joint disease, exercise-induced skeletal muscle injury, carpal tunnel syndrome, Guillan-Barre syndrome, Paget's disease of bone, ankylosing spondilitis, heterotopic bone formation; and Integumentary: solar radiation injury (including sunburn), thermal injury, chemical and contact dermatitis (including Rhus dermatitis), psoriasis, Bloom syndrome, leukoplakia (particularly oral), infectious dermatitis, Kaposi's sarcoma.

In another preferred embodiment, compositions comprising sulindac, R- and/or S-epimers, structural analogs or derivatives thereof, protect normal cells in a subject from damage caused by: aging, including age-related immune deficiency and premature aging disorders, cancer, cardiovascular disease, cerebrovascular disease, radiation injury, alcohol-mediated damage (including Wernicke-Korsakoffs syndrome), ischemia-reperfusion damage, inflammatory and auto-immune disease, drug toxicity, amyloid disease, overload syndromes (iron, copper, etc.), multi-system organ failure, and endotoxemia/sepsis.

In another preferred embodiment, compositions comprising sulindac, R- and/or S-epimers, structural analogs or derivatives thereof, protect normal cells in a subject from damage caused by ischemic/reperfusion damage to critical tissues such as the myocardium and central nervous system.

In another preferred embodiment, compositions comprising sulindac, R- and/or S-epimers, structural analogs or derivatives thereof, protect normal cells in a subject from cellular damage resulting from exposure to various chemical compounds which produce potentially damaging free radical species, comprising administering a therapeutically or prophylactically efficacious dosage of sulindac, R-epimer of sulindac, S-epimer of sulindac, derivatives, variants, structural analogs and mixtures thereof. The compositions of the invention are administered by a variety of routes, including parenterally, topically, and orally.

In another preferred embodiment, buffered aqueous solutions comprising a therapeutically or prophylactically efficacious dosage of sulindac, R-epimer of sulindac, S-epimer of sulindac, derivatives, variants, structural analogs and mixtures thereof is formulated for administration, typically by intravenous route, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, (7) hyperbaric oxygen, or (8) apoptosis of a predetermined cell population (e.g., lymphocyte apoptosis). The buffered aqueous solutions of the invention may also be used, typically in conjunction with other established methods, for organ culture, cell culture, transplant organ maintenance, and myocardial irrigation. Nonaqueous formulations, such as lipid-based formulations are also provided, including stabilized emulsions. The compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

In another aspect of the invention, compositions comprising sulindac, R-epimer of sulindac, S-epimer of sulindac, derivatives, variants, structural analogs and mixtures thereof, of the invention are employed to modulate the expression of naturally-occurring genes or other polynucleotide sequences under the transcriptional control of an oxidative stress response element (e.g., an antioxidant responsive element, ARE), such as an antioxidant response element of a glutathione S-transferase gene or a NAD(P)H:quinone reductase gene.

In other embodiments the invention provides methods for enhancing the recovery of skin of a warm-blooded animal from wounds, such as surgical incisions, burns, inflammation or minor irritation due to oxidative damage, etc. The methods comprise administering to the skin wound or irritation a therapeutically or, a prophylactically effective amount of a composition which comprises sulindac, R-epimer of sulindac, S-epimer of sulindac, derivatives, variants, structural analogs and mixtures thereof.

In preferred embodiments, the method is used for preventing, arresting, or treating (1) neurological damage such as Parkinson's disease or anoxia injury, (2) cardiac tissue necrosis resulting from cardiac ischemia, (3) autoimmune neurodegeneration (e.g., encephalitis), (4) acute lung injury such as in sepsis and endotoxemia, and (5) neuronal damage resulting from anoxia (e.g., stroke, drowning, brain surgery) or trauma (e.g., concussion or cord shock).

Compositions comprising sulindac, R-epimer of sulindac, S-epimer of sulindac, derivatives, variants, structural analogs and mixtures thereof, are also administered to individuals to prevent radiation injury or chemical injury by free radical generating agents. Military personnel and persons working in the nuclear, nuclear medicine, and/or chemical industries may be administered the compositions prophylactically. Compositions comprising sulindac, R-epimer of sulindac, S-epimer of sulindac, derivatives, variants, structural analogs and mixtures thereof, may also be used as chemoprotective agents to prevent chemical carcinogenesis; particularly by carcinogens which form reactive epoxide intermediates (e.g., benzo-[a]-pyrene, benzanthracene) and by carcinogens or promoting agents which form free radicals directly or indirectly (e.g., phenobarbital, TPA, benzoyl peroxide, peroxisome proliferators: ciprofibrate, clofibrate). Persons exposed to such chemical carcinogens are pretreated with compositions comprising sulindac, R-epimer of sulindac, S-epimer of sulindac, derivatives, variants, structural analogs and mixtures thereof to reduce the incidence or risk of developing neoplasia.

Compositions comprising sulindac, R-epimer of sulindac, S-epimer of sulindac, derivatives, variants, structural analogs and mixtures thereof, can also be formulated into a lipophilic base (or, if desired, an aqueous carrier) for topical application in cosmetics or sunburn-prevention creams and lotions. A typical cosmetic or sunburn-prevention cream or lotion will comprise about between 0.001 mg to 100 mg of sulindac, R-epimer of sulindac, S-epimer of sulindac, derivatives, variants, structural analogs and mixtures thereof, per gram of cosmetic or sunburn-prevention cream or lotion.

Compositions comprising sulindac, R-epimer of sulindac, S-epimer of sulindac, derivatives, variants, structural analogs and mixtures thereof, may also be administered to deep-divers or individuals exposed to hyberbaric environments were oxygen toxicity presents a health risk. Administration of an efficacious dose of compositions comprising sulindac, R-epimer of sulindac, S-epimer of sulindac, derivatives, variants, structural analogs and mixtures thereof, to an individual may permit the breathing or hyberbaric and/or oxygen-enriched gases with a reduced risk of oxygen toxicity. It is also believed that administration of an efficacious dosage of a composition comprising sulindac, R-epimer of sulindac, S-epimer of sulindac, derivatives, variants, structural analogs and mixtures thereof, can reduce toxicity and biological damage associated with exposure to ozone. Prophylactic administration of a composition comprising sulindac, R-epimer of sulindac, S-epimer of sulindac, derivatives, variants, structural analogs and mixtures thereof, to humans who are or will be exposed to ozone is expected to confer an enhanced resistance to ozone toxicity, such as the ozone-induced lung damage noted in geographical areas with high ozone levels (e.g., Los Angeles).

Cosmetic Formulations

The pharmaceutical/cosmetic compositions of the present invention formulated as solutions typically include a pharmaceutically- or cosmetically-acceptable organic solvent. The terms "pharmaceutically-acceptable organic solvent" and "cosmetically acceptable organic solvent" refer to an organic solvent which, in addition to being capable of having dispersed or dissolved therein the compositions comprising sulindac, R-epimer of sulindac, S-epimer of sulindac, derivatives, variants, structural analogs and mixtures thereof, also possesses acceptable safety (e.g. irritation and sensitization characteristics), as well as good aesthetic properties (e.g., does not feel greasy or tacky). The most typical example of such a solvent is isopropanol. Examples of other suitable organic solvents include: propylene glycol, polyethylene glycol (200-600), polypropylene glycol (425-2025), glycerol, 1,2,4-butanetriol, sorbitol esters, 1,2,6-hexanetriol, ethanol, butanediol, water and mixtures thereof. These solutions contain from about 0.001% to about 100%, preferably from about 0.001% to about 80%, compositions comprising sulindac, R-epimer of sulindac, S-epimer of sulindac, derivatives, variants, structural analogs and mixtures thereof, from about 0.001% to about 50%, and from about 1% to about 99 of an acceptable organic solvent.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972), incorporated herein by reference, contains numerous examples of suitable materials. Examples of classes of useful emollients include the following:

Hydrocarbon oils and waxes: Examples include mineral oil, petrolatum, paraffin, ceresin, ozokerite, microcrystalline wax, polyethylene, and perhydrosqualene.

Silicone oils: such as dimethyl polysiloxanes, methylphenyl polysiloxanes, water-soluble and alcohol-soluble silicone glycol copolymers.

Triglyceride esters: for example vegetable and animal fats and oils. Examples include castor oil, safflower oil, cottonseed oil, corn oil, olive oil, cod liver oil, almond oil, avocado oil, palm oil, sesame oil, and soybean oil.

Acetoglyceride esters: such as acetylated monoglycerides.

Ethoxylated glycerides: such as ethoxylated glyceryl monostearate.

Alkyl esters of fatty acids having 10 to 20 carbon atoms: Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, auryl lactate, myristyl lactate, and cetyl lactate.

Alkenyl esters of fatty acids having 10 to 20 carbon atoms: Examples include oleyl myristate, oleyl stearate, and oleyl oleate.

Fatty acids having 10 to 20 carbon atoms: Suitable examples include pelargonic, lauric, myristic, palmitic, stearic, isostearic, hydroxystearic, oleic, linoleic, ricinoleic, arachidic, behenic, and erucic acids.

Fatty alcohols having 10 to 20 carbon atoms: Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.

Fatty alcohol ether: Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.

Ether-esters: such as fatty acid esters of ethoxylated fatty alcohols.

Lanolin and derivatives: Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

Polyhydric alcohols and polyether derivatives: Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropyl sorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), C15-C18 vicinal glycol, and polyoxypropylene derivatives of trimethylolpropane are examples of this class of materials.

Polyhydric alcohol esters: Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Wax esters: such as beeswax, spermaceti, myristyl myristate, stearyl stearate.

Beeswax derivatives: e.g. polyoxyethylene sorbitol beeswax. These are reaction products of beeswax with ethoxylated sorbitol of varying ethylene oxide content, forming a mixture of ether-esters.

Vegetable waxes: including carnauba and candelilla waxes.

Phospholipids: such as lecithin and derivatives.

Sterols: Cholesterol and cholesterol fatty acid esters are examples thereof.

Amides: such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives.

Testing of Catalytic Antioxidant Compounds

The ability of any given molecule having a chemical structure including at least one methyl sulfoxide- and/or methyl sulfide-containing moiety, or at least one methionine and/or methionine sulfoxide moiety to act as a catalytic antioxidant can be determined empirically. For example, a molecule containing a methyl sulfoxide group to be tested (i.e., a test molecule) can be subjected to an enzymatic assay that indicates if the test molecule can serve as a substrate for MsrA, MsrB or other members of the Msr family (see, for instance, the NADPH assay described in Example 1, and the extraction assay described in Example 2, below). A test molecule can also be subjected to an assay that indicates the molecule's ability to increase resistance to oxidative stress in cells in vitro (for example PC-12 cells subjected to insult with MPP+) or in an animal subject, for example, *Drosophila* or a mammalian model of oxidative damage. See, for instance, the assays described in Examples 7, 8 and 9 below.

Preventing/Reversing Oxidative Damage in a Cell

The catalytic antioxidant compounds of the invention can be used to reduce, prevent or reverse oxidative damage in a cell (for example, a cell in an animal). In this method, a non-naturally occurring catalytic antioxidant compound is brought into contact with the cell. After entering the interior of the cell, the compound, if in the reduced (sulfide) form, will be oxidized to the sulfoxide by ROS (i.e., act as a ROS scavenger). Subsequent reduction catalyzed by an Msr enzyme will regenerate the original sulfide. If the test molecule contains a methyl sulfoxide moiety, it will be reduced to the sulfide by the Msr system within the cell and subsequently act as an antioxidant. With either the sulfide or the sulfoxide as the test molecule, the oxidation/reduction cycle will permit the compound to destroy ROS catalytically, as shown in FIG. 1.

The effectiveness of particular compounds can be assessed using conventional in vitro and in vivo assays, for example, determining a cell's, or an animal's response to a challenge with an agent that produces ROS. For instance, to assess a test molecule for the ability to prevent oxidative damage caused by ROS in a cell, cells can be cultured by conventional means and challenged with an agent that produces ROS within the cells. An exemplary cellular system for testing the effect of ROS damage in nerve cells, for example, is an assay employing PC-12 cells subjected to insult with MPP+, an agent that generates superoxide and other oxygen radicals. To assess the efficacy of a test compound in an animal, *Drosophila melanogaster* (fruit fly) is an excellent animal model. The flies can be treated with an agent that produces ROS (for example, paraquat) and then fed with a diet containing the test molecule and monitored for their survival, compared to control flies receiving Paraquat alone. Mammalian models of oxidative damage are also well known and include inter alia a transgenic mouse model of amyotrophic lateral sclerosis (ALS) based on a mutation in the superoxide dismutase (SOD1) gene.

Animal Subjects

Because oxidative damage to cells is a ubiquitous phenomenon, the invention is believed to be compatible with any animal subject. A non-exhaustive list of examples of such animals includes mammals such as mice, rats, rabbits, goats, sheep, pigs, horses, cattle, dogs, cats, and primates such as monkeys, apes, and human beings. Those animal subjects that have a disease or condition that relates to oxidative damage are preferred for use in the invention as these animals may have the symptoms of their disease reduced or even reversed. In particular, human patients suffering from inflammation, chronic obstructive lung diseases such as emphysema, reperfusion damage after heart attack or stroke, neurodegenerative diseases (for example, Parkinson's disease, Alzheimer's disease, and ALS), autoimmune diseases such as rheumatoid arthritis, lupus, and Crohn's disease, conditions related to premature birth, conditions caused by exposure to ultraviolet light, and age-related conditions (as but one example, age-related degenerative conditions of the eye including age-related macular degeneration and cataract formation) are suitable animal subjects for use in the invention. In the experiments described herein, animals used for demonstration of beneficial effects of protection against ROS damage by the compounds of the invention are the fruit fly and the mouse. Nonetheless, by adapting the methods taught herein to other methods known in medicine or veterinary science (for example, adjusting doses of administered substances according to the weight of the subject animal), the compounds and compositions of the invention can be readily optimized for use in other animals.

Formulations

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of, gels, lotions, and transdermal administration such as transdermal patches or iontophoresis devices. The term parenteral as used herein includes subcutaneous injections, intravenous, intramuscular, intrasternal injection, inhalation or infusion techniques.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

The methods and combinations of the present invention provide one or more benefits. Combinations of the present invention may allow for a lower dose of each agent. A benefit of lowering the dose of the compounds, compositions, agents and therapies of the present invention administered to a mammal includes a decrease in the incidence of adverse effects associated with higher dosages.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition of the invention can be administered to a subject either by themselves, or in pharmaceutical compositions where it is mixed with suitable carriers or excipient(s).

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

Depending on the specific protection being sought, for example, exposure to the sun, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to protection of normal cells against cancer with topical formulations of the composition, in other aspects of the invention the composition can be delivered by other methods. For example, the composition can be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. sulindac, peroxide, arsenic trioxide is facilitated. Without violating this constraint, the pH may be selected to improve the compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of the composition. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

Administration of Compositions

The catalytic antioxidant compositions of the invention may be administered to animals including humans in any suitable formulation. For example, the compositions may be formulated in pharmaceutically acceptable carriers or diluents such as physiological saline or a buffered salt solution. Suitable carriers and diluents can be selected on the basis of mode and route of administration and standard pharmaceutical practice. A description of other exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions, or enhance the activity of the Msr system. One such enhancing substance could be nicotinamide which is part of the molecule, NADPH, that supplies the reducing power to the reaction catalyzed by the members of the Msr family.

The compositions of the invention may be administered to animals by any conventional technique. Such administration may be oral or parenteral (for example, by intravenous, subcutaneous, intramuscular, or intraperitoneal introduction). The compositions may also be administered directly to the target site by, for example, surgical delivery to an internal or external target site, or by catheter to a site accessible by a blood vessel. Other methods of delivery, for example, liposomal delivery or diffusion from a device impregnated with the composition, are known in the art. The compositions may be administered in a single bolus, multiple injections, or by continuous infusion (for example, intravenously or by peritoneal dialysis). For parenteral administration, the compositions are preferably formulated in a sterilized pyrogen-free form.

Compositions of the invention can also be administered in vitro to a cell (for example, to prevent oxidative damage during ex vivo cell manipulation, for example of organs used for organ transplantation or in in vitro assays) by simply adding the composition to the fluid in which the cell is contained.

Effective Doses

An effective amount is an amount which is capable of producing a desirable result in a treated animal or cell (for example, reduced oxidative damage to cells in the animal or cell). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for parenteral or oral administration of compositions of the invention would be in the range of about 1 µg to 100 mg/kg of body weight in humans, the compositions of the invention would be in the range of about 0.1 mg/kg to 10 mg/kg of body weight in humans. An effective amount for use with a cell in culture will also vary, but can be readily determined empirically (for example, by adding varying concentrations to the cell and selecting the concentration that best produces the desired result). It is expected that an appropriate concentration would be in the range of about 0.0001-100 mM, preferably an appropriate concentration would be in the range of about 0.001-5 mM. More specific dosages can be determined by the method described below.

Toxicity and efficacy of the compositions of the invention can be determined by standard pharmaceutical procedures, using cells in culture and/or experimental animals to determine the $LD_{50}$ (the dose lethal to 50% of the population) and the $ED_{50}$ (the dose that effects the desired result in 50% of the population). Compositions that exhibit a large $LD_{50}/ED_{50}$ ratio are preferred. Although less toxic compositions are generally preferred, more toxic compositions may sometimes be used in in vivo applications if appropriate steps are taken to minimize the toxic side effects.

Data obtained from cell culture and animal studies can be used in estimating an appropriate dose range for use in humans. A preferred dosage range is one that results in circulating concentrations of the composition that cause little or no toxicity. The dosage may vary within this range depending on the form of the composition employed and the method of administration.

EXAMPLES

The present invention is further illustrated by the following specific examples, which should not be construed as limiting the scope or content of the invention in any way.

Example 1

Sulindac is a Substrate for MsrA Enzyme

The enzyme methionine sulfoxide reductase (MsrA) is known to exhibit specificity for substrates that contain a methyl sulfoxide group in the S configuration. This example provides evidence that sulindac, a known antioxidant containing a methyl sulfoxide moiety, can act as a substrate for MsrA.

Materials and Methods.

Reductase assay. With a purified Msr enzyme, sulindac reduction can be measured by a modified NADPH oxidation assay. Reaction mixtures were prepared containing 50 mM Tris-Cl pH 7.4, 15 μg of *E. coli* thioredoxin, 1 μg *E. coli* thioredoxin reductase, 100 nmoles of NADPH, 1 μmole of sulindac and 100-400 ng of MsrA in a final volume of 500 μl. Incubations were performed at 37° C. for various times.

The amount of product (sulindac sulfide) synthesized was determined by measuring the oxidation of NADPH spectrophotometrically at 340 nm. Because sulindac absorbs very strongly at this wavelength, the loss of absorbance at 340 nm could not be measured directly. To accomplish this, the sulindac and sulindac sulfide were removed from the incubations by extraction with ethyl acetate as follows. At the end of incubation, 500 μl of 0.5 M Bis-Tris-Cl pH 5.5 and 3 ml of ethyl acetate were added. The tubes were mixed (vortexed) for 5 seconds (3 times). After separation, the organic phase was removed and another 3 ml of ethyl acetate were added. After mixing the organic phase was again removed. The two extractions essentially removed all of the sulindac and sulindac sulfide, leaving the NADPH in the aqueous phase, which was measured at 340 nm. The loss of absorption at 340 nm, dependent on sulindac, is a measure of sulindac reduction. (Δ 0.062 at 340 nm=10 nmoles of sulindac sulfide formed).

Results: The results of a reductase assay using MsrA from *E. coli* are summarized below in Table 1.

Bacterial enzymes. Recombinant MsrA and MsrB from *Escherichia coli* were obtained as described previously (Grimaud, R. et al., J. Biol. Chem. 276 (2001) 48915-48920; Rahman, M. A. et al., Cellular & Molecular Biology 38 (1992) 529-542). Partially purified DEAE fractions of free-S-Msr (fSMsr), free-R Msr (fRMsr) and MsrA1, and a membrane vesicle associated Msr (mem-R,S-Msr) were prepared from an *E. coli* MsrA/B double mutant as described (Etienne, F. et al., Biochem. & Biophys. Res. Comm. 300 (2003) 378-382; Spector, D. et al., Biochem. & Biophys. Res. Comm. 302 (2003) 284-289). The enzyme preparations had specific activities similar those reported earlier.

Mammalian enzymes. Calf liver, kidney and brain extracts were prepared at 4° C. Thirty grams each of calf tissue (liver, kidney, brain) were minced using a hand-held homogenizer in 5 volumes of buffer A containing 250 mM sucrose, 10 mM Tris-Cl pH 7.4 and 1 mM EDTA. The homogenates were dounced (6 strokes) and spun at 1,500×g for 10 minutes and the pellet was discarded. The supernatants (S-10) were spun at 10,000×g for 10 minutes. The S-10 supernatants were centrifuged at 100,000×g for 12 hours and the resulting pellets and supernatants (S-100) were saved. The S100 pellets were suspended in cold buffer A and centrifuged at 100,000×g for 4 hours. The washed microsomal pellets (containing all of the ribosomes) were suspended in 2 ml of buffer A (S-100 pellet).

To prepare mitochondria, the S10 pellets were suspended in 20 ml buffer A. The suspension was layered on top of a discontinuous Ficoll gradient made up of an equal volume of 12% Ficoll in buffer A (lower layer) and 7.5% Ficoll in buffer A (upper layer). The tubes were centrifuged at 24,000×g for 24 min. The pellets were resuspended in buffer A and centrifuged at 20,000×g for 15 min. The pellets (containing mitochondria) were suspended in 2 ml of buffer A. All fractions were stored at −80° C.

TABLE 1

Reduction of Sulindac to Sulindac Sulfide by MsrA

| Tube # | MsrA (100 ng/μl) | Sulindac (0.2M) | Thioredoxin (5 μg/μl) | MetS(O) (0.2M) | Time (min) | $OD_{340}$ | Δ $OD_{340}$ | Sulindac sulfide (nmol) |
|---|---|---|---|---|---|---|---|---|
| 1 | 8 μl | — | 3 μl | — |  | 0.657 |  | 0 |
| 2 | — | 5 μl | 3 μl | — |  | 0.660 |  | 0 |
| 3 | 1 μl | 5 μl | 3 μl | — | 20 | 0.622 | 0.038 | 5.8 |
| 4 | 2 μl | 5 μl | 3 μl | — | 20 | 0.586 | 0.074 | 11.2 |
| 5 | 4 μl | 5 μl | 3 μl | — | 20 | 0.522 | 0.138 | 21.0 |
| 6 | 2 μl | 5 μl | — | — | 20 | 0.684 |  |  |
| 7 | 2 μl | 5 μl | 3 μl | — | 10 | 0.626 | 0.034 | 5.2 |
| 8 | 2 μl | 5 μl | 3 μl | — | 30 | 0.531 | 0.129 | 19.4 |

The results show that sulindac was reduced in a time- and concentration-dependent manner by MsrA enzyme.

Example 2

Sulindac is a Substrate for Msr Enzymes in Bacteria and Mammals

This example demonstrates that sulindac is a substrate for MsrA and membrane-bound Msr in *E. coli* and for MsrA and possibly other Msr enzymes in mammalian tissues.

Material and Methods.

Chemicals, enzymes and substrates. Sulindac (S), sulindac sulfide (SS) and all other chemicals and *E. coli* thioredoxin reductase were obtained from Sigma Chemicals (St. Louis, Mo.), unless noted otherwise. Thioredoxin (from *E. coli*) was purchased from Promega (Madison, Wis.). N-acetyl-$^3$H-met-R,S—(O), met-R—(O), met-S—(O) DABS-met-R—(O) and DABS-met-S—(O) were prepared as previously described (Brot N. et al., Anal. Biochem. 122 (1982) 291-294; Lavine, F. T. J. Biol. Chem. 169 (1947) 477-491; Minetti G. et al., Ital. J. Biochem. 43 (1994) 273-283).

Reductase assay and quantitation of sulindac sulfide formed. With crude cellular fractions when there is a large amount of NADPH oxidation, the NADPH assay described in Example 1 above cannot be used. For use with crude cellular fractions, an extraction assay was developed based on the ability of sulindac sulfide to be extracted into benzene. The reaction mixture for the reduction of sulindac to sulindac sulfide contained in a total volume of 30 μl: 100 mM Tris-Cl, pH 7.4; 0.6 μmoles glucose-6-phosphate; 50 ng glucose-6-phosphate dehydrogenase; 30 nmoles NADPH; 2.5 μg thioredoxin, 1 μg thioredoxin reductase, 50 nmoles sulindac and varying amount of Msr enzymes. Unless stated otherwise, incubations were for 1 hour at 37° C. At the end of the incubation 370 μl of 25 mM Tris-Cl pH 8.0, 100 μl acetonitrile and 1 ml of benzene were added to each tube. After vortexing for 30 seconds and spinning for 1 min at room temperature, the benzene phase was removed and the optical density was read at 350 nm. Fifty nmoles of Sulindac (S) or sulindac sulfide (SS), when carried through the extraction procedure, gave optical density readings of 0.910 and 0.030, respectively. Under these conditions, virtually all of the sulindac sulfide was extracted into the benzene, while about 2.5% of sulindac was extracted. In some experiments using calf tissue extracts, the standard 30 μl reaction mixture volume was tripled (90 μl) to obtain statistically significant values. The extraction assay was not altered except for reduction of the Tris buffer volume to 310 μl.

To remove the S epimer of sulindac, sulindac (R,S mixture) was incubated with excess MsrA (4 μg) and DTT for 60 minutes, or until the reaction reached completion. Upon completion, any further reduction seen upon addition of an enzyme fraction in a second incubation would be due to reduction of the R epimer of sulindac.

In some experiments the product was also identified by thin layer chromatography (TLC). After incubation, both the unreacted Sulindac (S) and sulindac sulfide (SS) product were extracted into 1 ml ethyl acetate. The ethyl acetate phase was removed, dried in a speed vacuum at room temperature and the residue was suspended in 5 μl of ethyl acetate which was then loaded onto a TLC plate. The plate was developed with butanol:acetic acid:water (60:15:25) as the solvent. The compounds were visualized by their yellow color. The Rf values of sulindac and sulindac sulfide were 0.80 and 0.95, respectively.

Results.

Figure 3A:
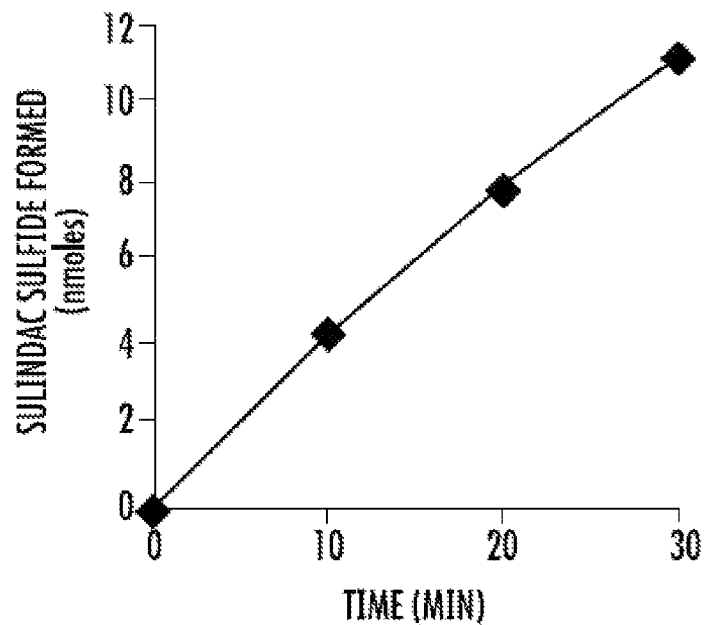
FIGS. 3A and 3B are two graphs showing kinetics of sulindac sulfide production by MsrA, according to an embodiment of the invention.
Figure 3B:
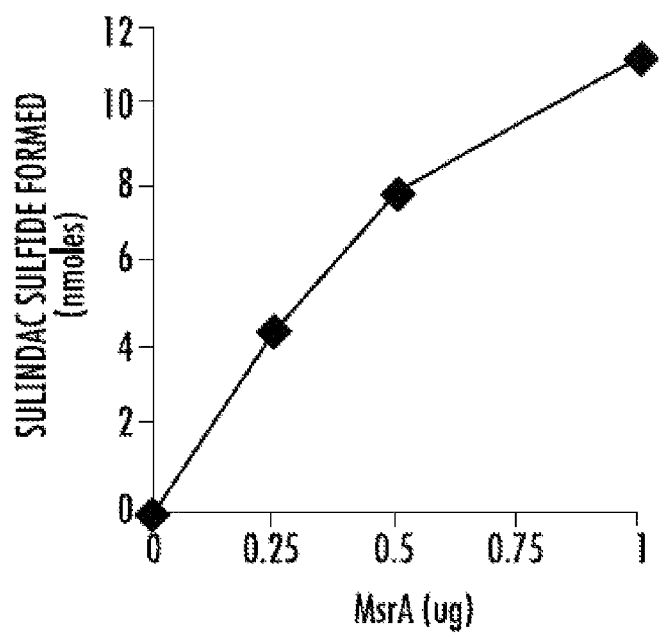

Using the extraction assay described above in Methods, it was found that recombinant MsrA from $E.\ coli$ could reduce sulindac to sulindac sulfide. FIG. 3A shows a time course for the reaction and FIG. 3B shows the effect of MsrA concentration on reduction of sulindac. The reaction was dependent on the thioredoxin reducing system. The product, sulindac sulfide, was independently identified by TLC.

Sulindac is a substrate for mem-R,S-Msr. $E.\ coli$ is known to have at least 6 members of the Msr family. Referring to Table 2, these proteins differ in their stereo-specificity, substrate specificity, i.e., free vs. protein-bound Met(O), and location within the cell, i.e., soluble or membrane-associated. Whereas the msrA and msrB genes have been cloned and the recombinant proteins purified, the other soluble $E.\ coli$ Msr enzymes (i.e., fSMsr, fRMsr and MsrA1) have been only partially purified, but have been separated by conventional fractionation procedures using DEAE cellulose chromatography (Etienne, F. et al., Biochem. & Biophys. Res. Comm. 300 (2003) 378-382; Spector, D. et al., Biochem. & Biophys. Res. Comm. 302 (2003) 284-289). The membrane associated Msr (i.e., mem-R,S Msr), which has activity toward both the R and S forms of free and peptide bound met(o), was present as a membrane vesicle preparation.

TABLE 2

Substrate Specificity of Methionine Sulfoxide Reductases in $E.\ coli$

| ENZYME TYPE | SUBSTRATE | | | |
|---|---|---|---|---|
| | Free-R—(O) | Free-S—(O) | Peptide-R—(O) | Peptide-S—(O) |
| MsrA | | + | | + |
| MsrB | (+) | | + | |
| fRMsr | + | | | |
| fSMsr | | + | | |
| MsrA1 | | | | + |
| Membrane Msr | + | + | + | + |

Brackets ( ) indicate a very weak activity.

Referring to Table 3, sulindac was compared as a substrate for highly purified MsrA and MsrB from $E.\ coli$ and the partially purified enzyme preparations. The results showed that MsrA and the mem-R,S-Msr are able to reduce sulindac to sulindac sulfide. Very weak activity was observed with MsrA1. Sulindac was not a substrate for MsrB, which recognizes peptide-bound Met-S—(O).

TABLE 3

Activity of $E.\ coli$ Msr Enzymes Using Sulindac as a Substrate.

| ENZYME TYPE | UNITS OF ACTIVITY |
|---|---|
| MsrA | 11.3 |
| MsrB | 0 |
| fRMsr | 0 |
| fSMsr | 0 |
| MsrA1 | <0.9 |
| Membrane | 5.1 |

Unit of activity is defined as nmoles of SS formed per hour.
Enzyme concentrations used: 250 ng MsrA; 10 μg MsrB; 290 μg fRMsr; 200 μg fSMsr; 40 μg MsrA1; 50 μg membrane fraction.

Referring now to Table 4, it is seen that the membrane bound Msr of $E.\ coli$, which likely contains more than one Msr activity, reduces primarily the R form of sulindac. In these experiments either sulinadac, which is a mixture of the R and S epimers, or the R epimer of sulindac (see Methods) were used as substrates. Both exhibited similar activities. Although these results support the R form being reduced, definitive proof may require the chemical synthesis and assay of each epimer of sulindac.

TABLE 4

Membrane Msr of $E.\ coli$ Reduces Primarily the R Epimer of Sulindac.

| SUBSTRATE | NMOLES FORMED |
|---|---|
| Sulindac (R, S) | 2.75 |
| Sulindac (R) | 2.41 |

R epimer of sulindac was obtained by incubating sulindac (R, S) with excess MsrA as described in Methods to remove the S epimer.
35 μg of membrane fraction was used.

Reduction of sulindac in mammalian (bovine) tissues. Results shown in Table 5 reveal that crude homogenates (S-10 fractions, see Methods) of calf liver, kidney and brain are able to reduce sulindac. Of the tissues tested, kidney has the highest specific activity, and brain the lowest.

TABLE 5

Sulindac Reductase Activity in Calf Tissues.

| TISSUE | SPECIFIC ACTIVITY |
|---|---|
| Liver | 4.39 |
| Kidney | 6.53 |
| Brain | 2.31 |

The preparation of the various S-10 fractions are described in Methods.
Specific activity is given as nmoles of product formed per hour per mg of protein.

The liver extracts were fractionated and mitochondria, S-100 and S-100 pellet (microsomes) were prepared as described in Methods. As shown in Table 6, all three cellular fractions were able to reduce sulindac to sulindac sulfide. The identity of the enzyme(s) responsible for the activity was not determined, but preliminary evidence indicated that MsrA was largely responsible, based on the observation that the addition of excess amounts of Met-S—(O) inhibited the activity in all three fractions, whereas the addition of Met- R—(O) had only a slight effect. Thus the responsible enzyme had Met-S—(O) activity. Because free Met(O) Msr enzymes (i.e., FSMsr and FRMsr) cannot reduce sulindac (Table 2), MsrA is most likely the enzyme responsible for this activity.

TABLE 6

Subcellular Distribution Sulindac Reductase Activity in Bovine Liver.

| LIVER FRACTIONS | SPECIFIC ACTIVITY |
| --- | --- |
| S-10 | 4.39 |
| S-100 | 6.20 |
| Mitochondria | 2.44 |
| Microsomes | 1.31 |

The indicated liver fractions were prepared as described in Methods.
Specific activity is given as nmoles of product synthesized per hour per mg of protein.

Example 3

Synthesis of Sulindac Methionine Catalytic Antioxidants

As shown above, sulindac is a substrate for MsrA but not for MsrB. Sulindac contains a methyl sulfoxide moiety which is recognized by MsrA enzymes, but does not contain a N-methionine sulfoxide moiety (see FIG. 2), the substrate recognized by both MsrA and MsrB enzymes (Table 2). This example describes schemes for the chemical synthesis of derivatives of sulindac that are improved as substrates for multiple Msr enzymes including MsrB, by modification to contain an N-substituted methionine, in which the methionine amino group is in peptide or amide linkage.

Figure 4A:
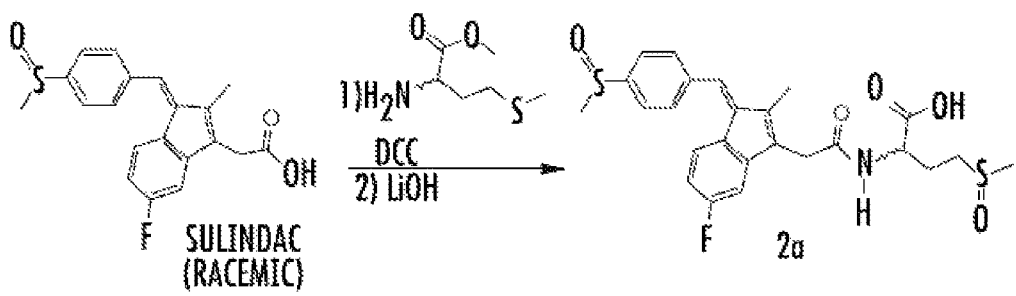
FIGS. 4A and 4B are schematic diagrams showing chemical synthetic pathways for making methionine derivatives of sulindac (compounds 2a and 3a), according to an embodiment of the invention.
Figure 8:
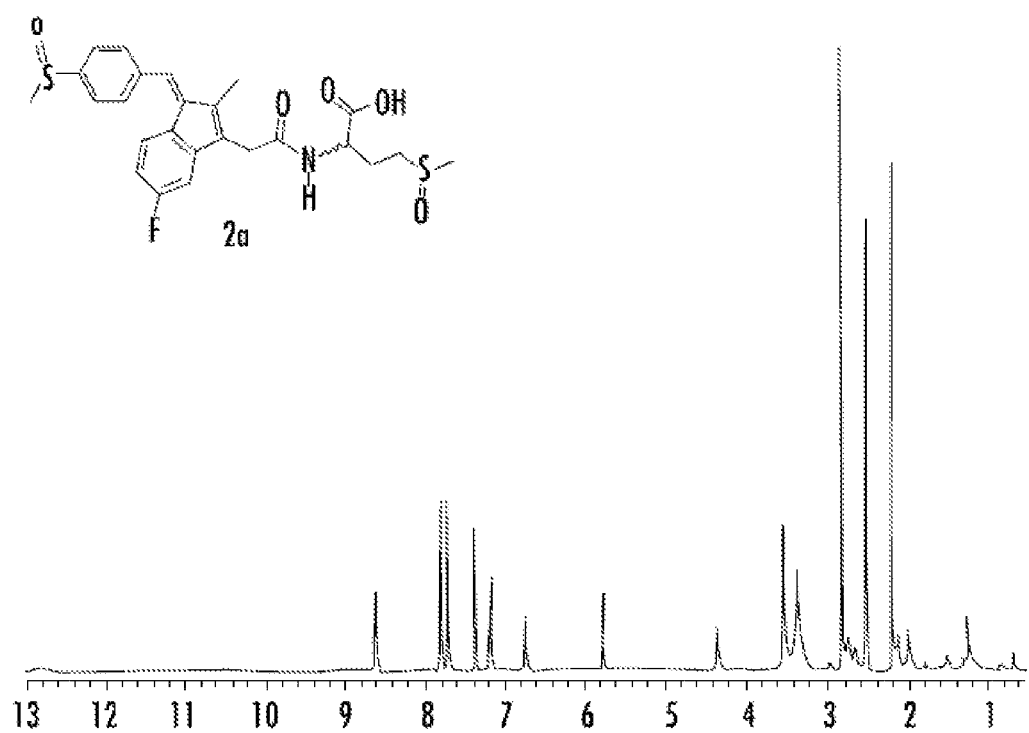
FIG. 8 shows a NMR spectrum of compound 2a of the invention.

Referring to FIG. 4A, compound 2a (1(Z)-5-fluoro-2-methyl-1-[4-(methylsulfinyl)phenyl]methylene]-1H-indene-3-[1-methylthiomethylenyl-2-aminoacetyl]propanoic acid) is shown. Compound 2a contains a methionine group linked through the amino group to the acetyl moiety of sulindac. This compound was synthesized starting from sulindac and methionine sulfoxide methyl esters as follows. To a 50 ml round bottom flask under an argon atmosphere fitted with a teflon stir bar and rubber stopper, 1.4 mmol of sulindac was dissolved in 20 ml DMF followed by the addition of 1.5 mol of methionine sulfoxide methyl ester. Dicyclohexylcarbodiimide (1.2 mmol), triethylamine (2.0 mmol) and 4-dimethylaminopyridine (0.05 mmol) were placed in the reaction flask. After 12 hours, TLC analysis (75% ethyl acetate in hexanes) showed the formation of the product at $R_f$=0.29. The reaction mixture was then placed onto a 2.5 cm diameter flash column filled with approximately 6 inches of silica gel and topped off with a quartz sand plug. The following elution sequence was used: 5% EtOAc/Hex (250 mL), 30% EtOAc/Hex (500 mL), 50% EtOAc/Hex (250 mL) and a final elution of 85% EtOAc/Hex (250 mL). HPLC analysis of the compound (gradient elution from 5% to 95% MeCN/$H_2O$ over 45 min) gave a peak at 22.5 min with 98% purity. Proton NMR analysis of compound 2a is shown in FIG. 8.

Figure 4B:
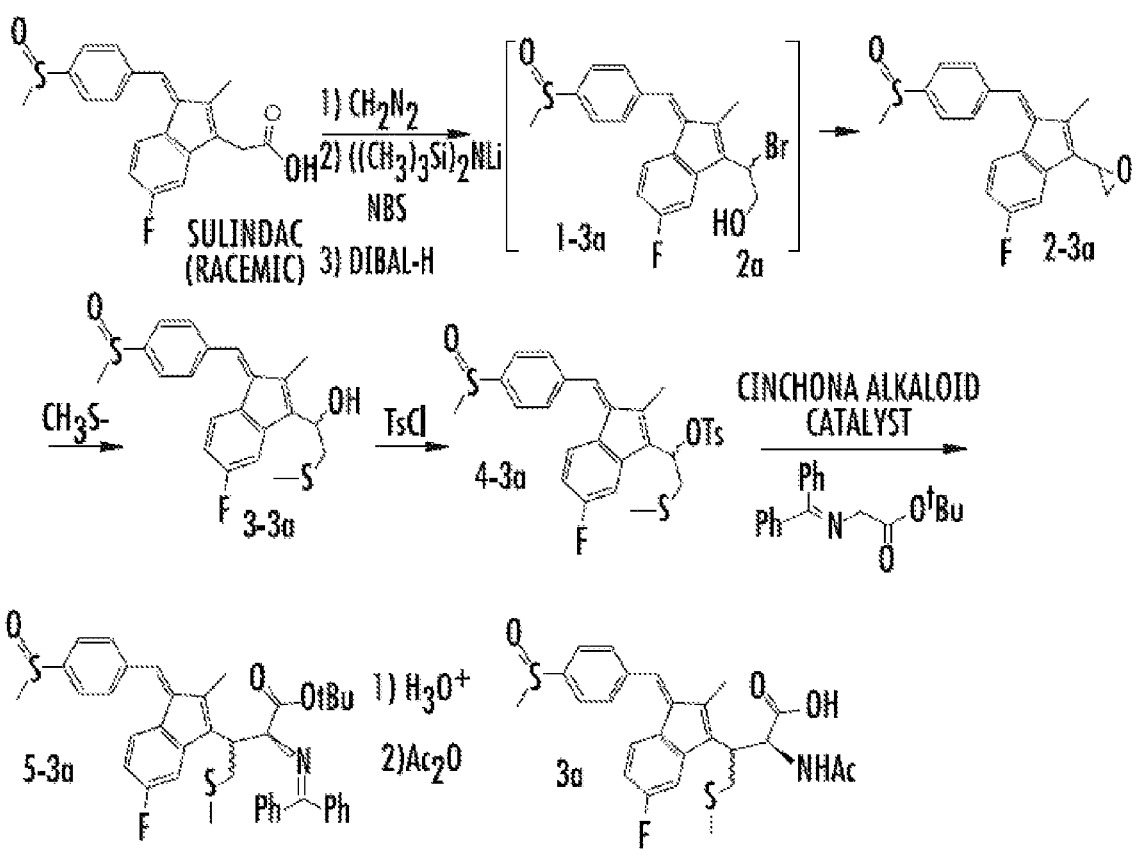

Another methionine derivative of sulindac, i.e., compound 3a, is given in FIG. 4B. A suitable scheme for the synthesis of compound 3a, with control of the α-carbon stereochemistry, is shown. In this particular synthetic method, the synthesis begins with commercially available sulindac (racemic form). The sulindac is converted to its methyl ester by treatment with diazomethane ($CH_2N_2$). The methyl ester is then treated with a strong base to form the enolate, followed by quenching with N-bromosuccinimide (NBS) leading to the α-bromoester (Kita et al., J. Am. Chem. Soc. 123:3214, 2001). The ester group of this intermediate is then selectively reduced to the primary alcohol using diisobutylaluminum hydride (DIBAL-H), according to the method of Fukuyama et al., J. Am. Chem. Soc. 116:3125, 1994, to give intermediate compound 1-3a. Compound 1-3a epoxidizes to give intermediate compound 2-3a. Treatment of compound 2-3a with methyl sulfide is expected to lead to the β-hydroxysulfide compound 3-3a (Conte et al., Tetrahedron Lett. 30:4859, 1989). Using paratoluene sulfonylchloride (TsCl), the hydroxyl group in compound 3-3a is converted to the corresponding tosylate (compound 4-3a). By an extension of the method of O'Donnell (O'Donnell et al., J. Am. Chem. Soc. 111:2353, 1989), the tosylate on compound 4-3a reacts with a protected diphenylimino-glycine derivative under the influence of a cinchona alkaloid asymmetric phase-transfer catalyst. This reaction gives the corresponding α-imino ester (compound 5-3a), with control over the stereochemistry of the α-carbon. Subsequent aqueous hydrolysis of the imino and tert-butyl ester groups gives the desired compound 3a.

Figure 5A:
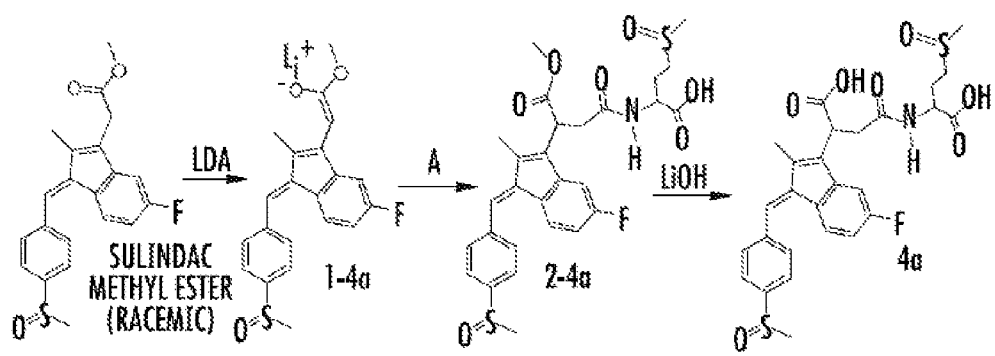
FIGS. 5A and 5B are schematic diagrams showing chemical synthetic pathways for making methionine derivatives of sulindac (compounds 4a and 5a), according to an embodiment of the invention.

Referring now to FIG. 5A, sulindac contains a methylene group adjacent to a carboxyl that is easily converted into enolate 1-4a. Lithium diisopropylamide (LDA) is a base typically used to form these types of enolates. Intermediate 1-4a should react with bromoacetyl methionine sulfoxide (A) to form the new carbon-carbon bond found in 2-4a. Hydrolysis of this intermediate with lithium hydroxide gives the corresponding carboxylic acid derivative (compound 4a).

Figure 5B:
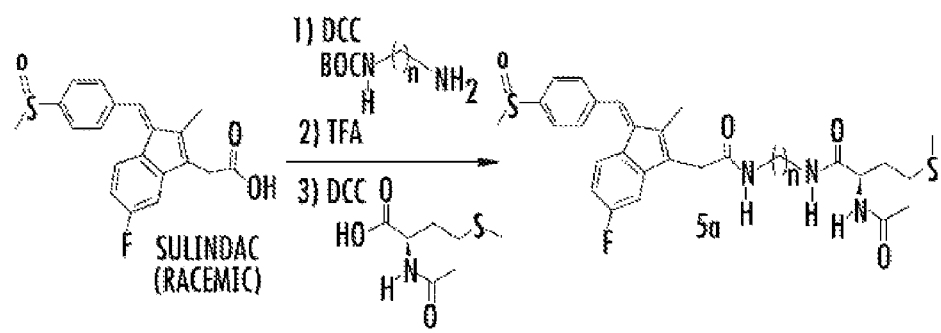

FIG. 5B illustrates yet another embodiment of an N-methionine derivative of sulindac indicated as compound 5a. In compound 5a, the sulindac structure and the N-acetyl methionine group are tethered by a diamine chain that can be of varying length. The use of such a linker molecule provides the ability to generate a large variety of methionine derivatives through combinatorial synthesis methods. Compound 5a may be obtained as follows (FIG. 5B). Under the action of DCC, sulindac is coupled to tert-butoxycarbonyl (BOC) mono-protected diamine, followed by removal of the BOC protecting group under acidic conditions using trifluoroacetic acid (TFA). This intermediate is coupled to N-acetyl methionine in the presence of DCC to give compound 5a. Compound 5a can easily be obtained as the single enantiomer (or epimers of the sulfoxide position). The addition of N-acetyl methionine moieties is preferred, as these moieties are expected to act as a substrate for enzymes that recognize N-blocked methionine sulfoxide, (such as MsrA and MsrB). D amino acids may be preferred to minimize metabolism. A racemic mixture of the sulfoxides (i.e., both R and S forms) is preferred if it is desired to have the compound function as a substrate for most, if not all, known Msr family enzymes that recognize free or protein-bound forms of methionine sulfoxide (whether R or S epimers).

Example 4

Synthesis of Methionine Catalytic Antioxidants Derived from Salicylic Acid and Mefenamic Acid This example describes chemical synthetic schemes suitable for preparing bifunctional compounds that can serve both as catalytic antioxidants and anti-inflammatory agents (COX inhibitors).

As described above, sulindac is one example of a COX inhibitor. This example describes methionine derivatives of other COX inhibitors, i.e., acetyl salicylic acid and mefenamic acid. These bifunctional antioxidant compounds contain the amino group of methionine in the form of an amide and preferably retain the carboxyl group found in the parent compounds that may be critical to their inhibitory action.

Figure 6A:
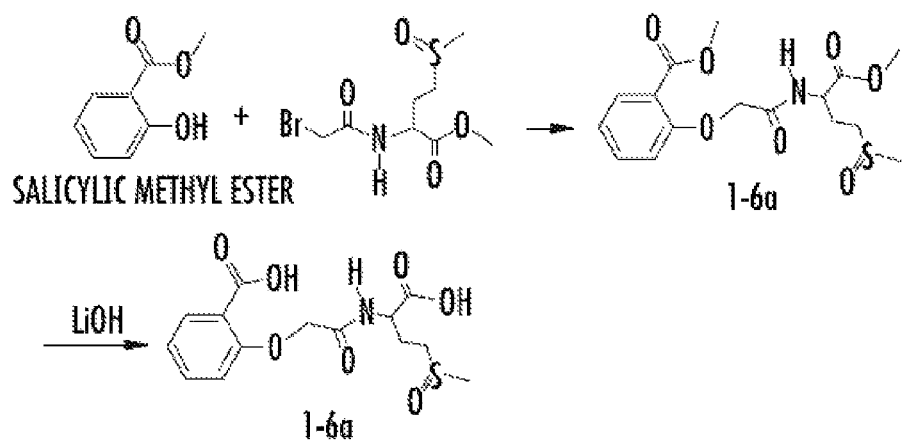
FIGS. 6A and 6B are schematic diagrams showing chemical synthetic pathways for making catalytic antioxidants based on salicylic acid and mefenamic acid (compounds 6a and 7a, respectively), according to an embodiment of the invention.
Figure 6B:
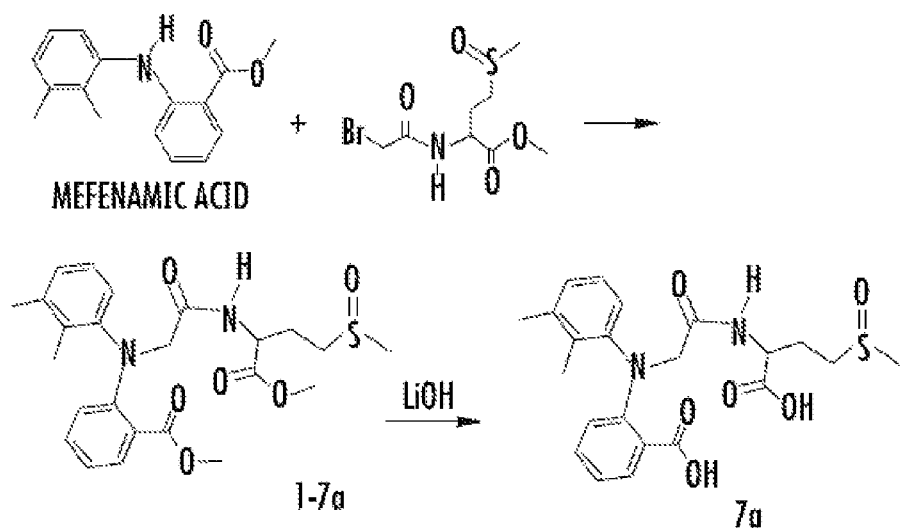

Referring to FIG. 6A, starting from the methyl ester of salicylic acid, the phenol hydroxy group is shown to react with the carbon bearing the bromine in bromoacetylmethionine sulfoxide (BAMS) to form the oxygen-carbon bond of intermediate 1-6a. In the case of mefenamic acid, the reaction with BAMS is shown to occur at the amine nitrogen to give intermediate 1-7a (FIG. 6B). The salicyclic and mefenamic methionine sulfoxide derivatives can be converted to the respective carboxylic acid products 6a and 7a using a mild hydrolysis reaction with lithium hydroxide (LiOH).

Example 5

Synthesis of Methionine Catalytic Antioxidants Derived from Ibuprofen, Indomethacin and Rofecoxib/Vioxx®

Figure 7A:
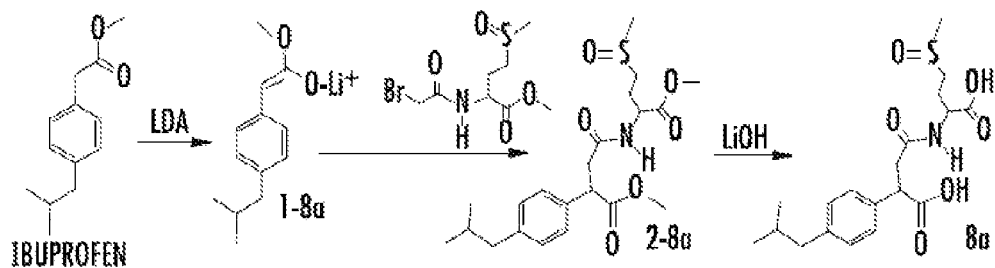
FIGS. 7A-C are schematic diagrams showing chemical synthetic pathways for making catalytic antioxidants based on ibuprofen, indomethacin and Vioxx® (compounds 8a, 9a, and 10a, respectively), according to an embodiment of the invention.
Figure 7B:
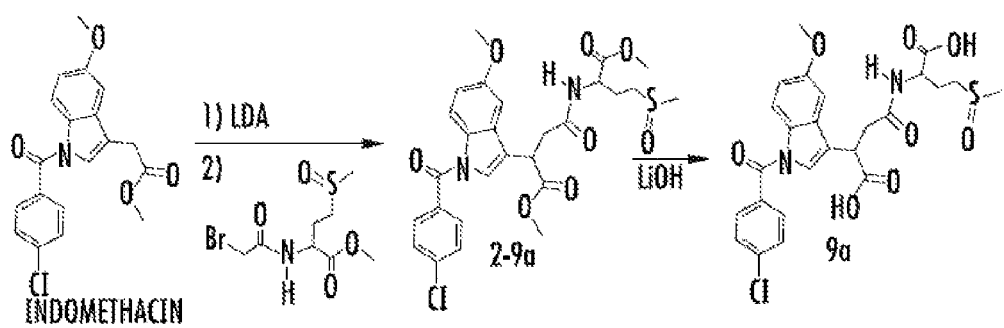
Figure 7C:
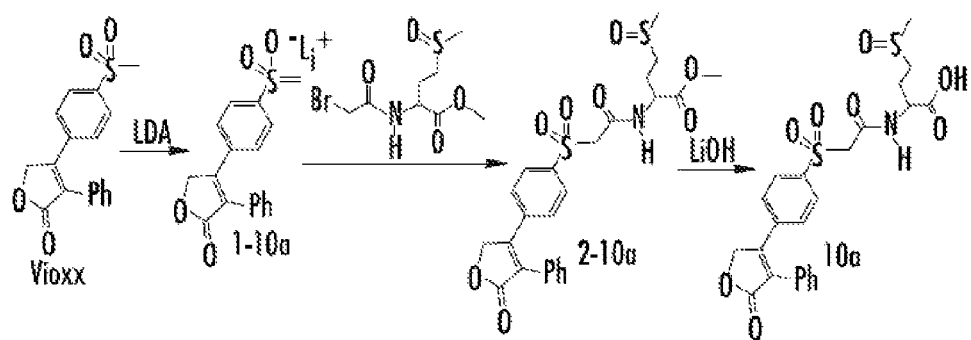

Referring now to FIG. 7, ibuprofen (FIG. 7A), indomethacin (FIG. 7B), and rofecoxib/Vioxx® (FIG. 7C) each contain a methylene group adjacent to a carboxyl or a sulfonyl group that is easily converted into enolate, shown for intermediates 1-8a and 1-10a. Lithium diisopropylamide (LDA) is a typical base used to form enolates. Intermediates 1-8a, 1-9a, and 1-10a are shown to react with bromoacetyl methionine sulfoxide to form the new carbon-carbon bonds in intermediates 2-8a, 2-9a, and 2-10a. Hydrolysis of these intermediates with lithium hydroxide gives the corresponding carboxylic acid derivatives (compounds 8a, 9a, and 10a).

Example 6

Sulindac Methionine Sulfoxide is a Substrate for MsrA and MsrB

As shown above, sulindac is a substrate for MsrA but not for MsrB. Referring to FIG. 4A, unmodified sulindac contains a methyl sulfoxide moiety, but does not include within its structure a methionine sulfoxide moiety, the required substrate for Msr B enzymes. Sulindac methionine sulfoxide (SMO), an N-acetyl methionine sulfoxide derivative of sulindac described in Example 4 above includes both a methyl sulfoxide and a methionine sulfoxide (see, for instance, compound 2a in FIG. 4A). This example demonstrates that SMO can serve as a substrate for both MsrA and MsrB enzymes.

Materials and Methods.

Synthesis of SMO. Sulindac methionine sulfoxide (SMO) was synthesized according to the synthetic pathway described in Example 3 supra. Compound 2a was used for these experiments.

Reductase assay and thin layer chromatography (TLC). Reaction mixtures were prepared in duplicate for assay of the reduction of sulindac (S) and sulindac methionine sulfoxide (SMO). Mixtures contained in a total volume of 30 µl: 100 mM Tris-Cl pH 7.4, 15 mM DTT, 100 nmoles of S or SMO, 3 µg of MsrA enzyme, or 21 µg of MsrB enzyme. Incubation was carried out for 2 hours at 37° C., at the end of which the duplicate samples were combined and dried in a speed-vacuum unit at room temperature. The residue was suspended in 50 µl of ethanol, which was then loaded onto a silica gel TLC plate. The plate was developed with butanol: acetic acid:water (60:15:25) as the solvent. The compounds were visualized by their yellow color.

Results:

As discussed above, it is known that MsrA can reduce methyl sulfoxide moieties that occur as functional groups within free and peptide-bound methionine (i.e., Met(O)), but also within other molecules. By contrast, MsrB can only reduce Met(O), and works best with Met(O) in peptide linkage (see Table 2). Accordingly, based on the known substrate specificity of MsrA and MsrB, several different products would be predicted upon reaction of sulindac and SMO with MsrA and MsrB. For example, because the structure of sulindac (S) contains only a methyl sulfoxide (as seen in FIG. 2), reduction of S by MsrA results in sulindac sulfide. Reduction of sulindac by MsrB would not be expected to generate a product, due to the absence of methionine sulfoxide in sulindac. In contrast to unmodified sulindac, SMO includes both the methyl sulfoxide group of sulindac as well as the methyl sulfoxide included in the methionine group (see, for example, compound 2a in FIG. 4A). Accordingly, reaction of SMO with MsrA could generate several possible products having one or the other, or both methyl sulfoxide groups reduced, i.e.: sulindac sulfide methionine sulfoxide (SSMO), sulindac methionine (SM), or sulindac sulfide methionine (SSM). With MsrB, however, only the methionine sulfoxide should be reduced and the expected product is SM.

Figure 9:
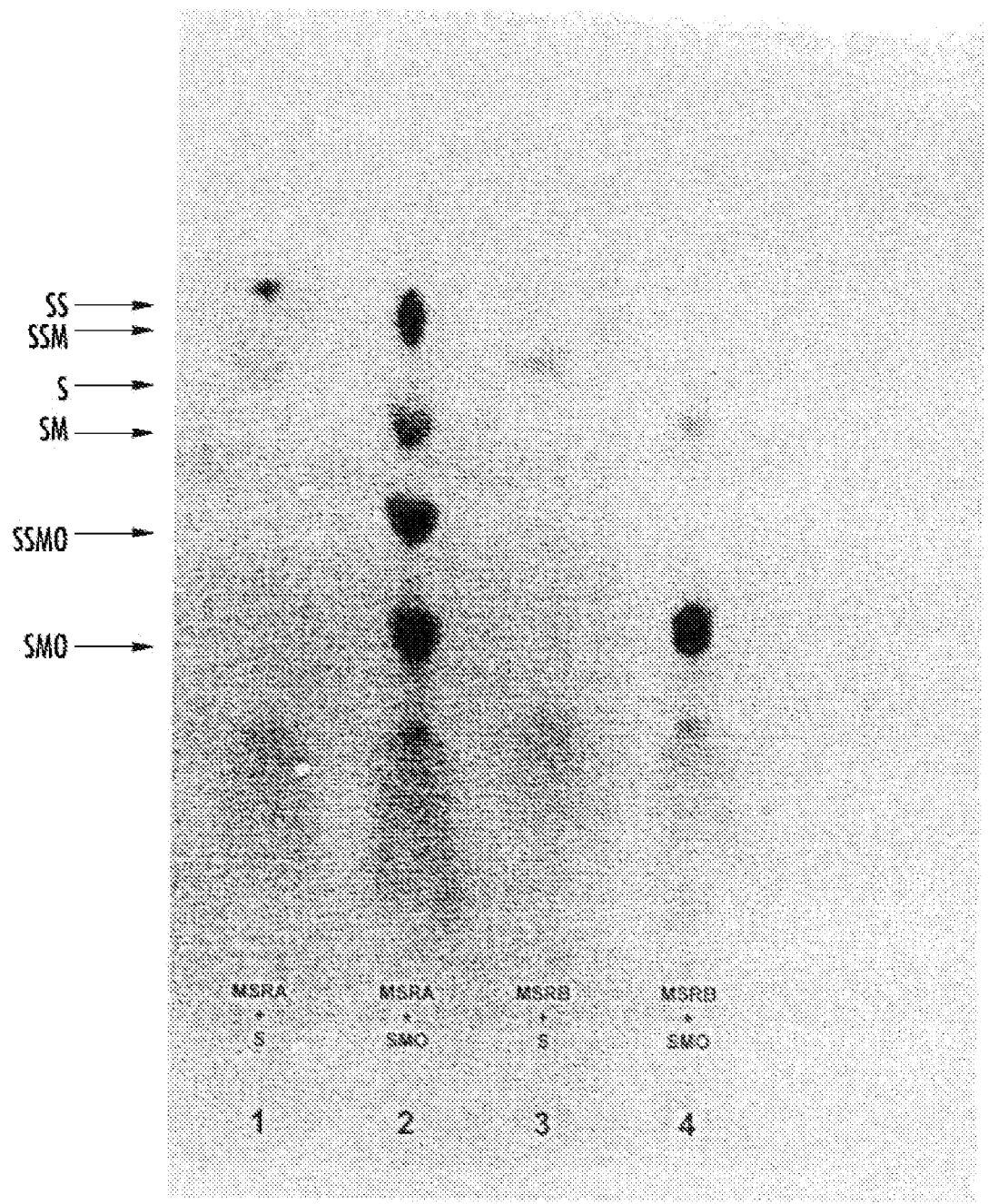
FIG. 9 is a micrograph of a TLC plate showing the presence of reduction products of sulindac (S) and sulindac methionine sulfoxide (SMO) following incubation with MsrA and MsrB enzymes. Results demonstrate that S is a substrate for MsrA and that SMO is a substrate for both MsrA and MsrB.

FIG. 9 shows TLC results from the various incubations, i.e., MsrA+S (lane 1); MsrA+SMO (lane 2); MsrB+S (lane 3) and MsrB SMO (lane 4). In FIG. 9, the indicated substrates and reaction products are as follows: S—sulindac; SS—sulindac sulfide; SM—sulindac methionine; SSM—sulindac sulfide methionine; SMO—sulindac methionine sulfoxide; SSMO—sulindac sulfide methionine sulfoxide. The positions where the substrates, products and standards migrate on the TLC plate are indicated by arrows.

The results of the enzyme assays demonstrate the following. Lane 1 shows the presence of SS, indicating that sulindac is a substrate for MsrA. Lane 2 reveals formation of SSM, SM, and SSMO, demonstrating that SMO is a substrate for MsrA and that both methyl sulfoxide groups can be reduced. Lane 3 shows only S, demonstrating that unmodified sulindac is not a substrate for MsrB. By contrast, lane 4 reveals that SMO is a substrate for MsrB, shown by the formation of SM (FIG. 9). Thus it is shown that a methionine derivative of sulindac, i.e., SMO, can act as a substrate for both MsrA and MsrB enzymes.

Example 7

Sulindac Increases Resistance to Oxidative Stress in *Drosophila*

This example demonstrates that sulindac, an antioxidant containing a methyl sulfoxide moiety, can extend the lifespan of flies subjected to an agent known to kill flies via production of ROS.

Materials and Methods.

Paraquat is a cytotoxic compound known to form superoxide radicals intracellularly. Three different concentrations of paraquat (i.e., 2.5 mM, 5 mM and 10 mM) were tested. Flies (*Drosophila*) were raised for 3 days on apple juice medium (33% apple juice, 1.7% sucrose and 2.7 mg/ml methyl paraben, a mold inhibitor, in 3.5% agar) containing various concentrations of sulindac or no supplement (Controls). After 3 days at 25° C., flies were transferred to test vials for counting.

Results.

Figure 10:
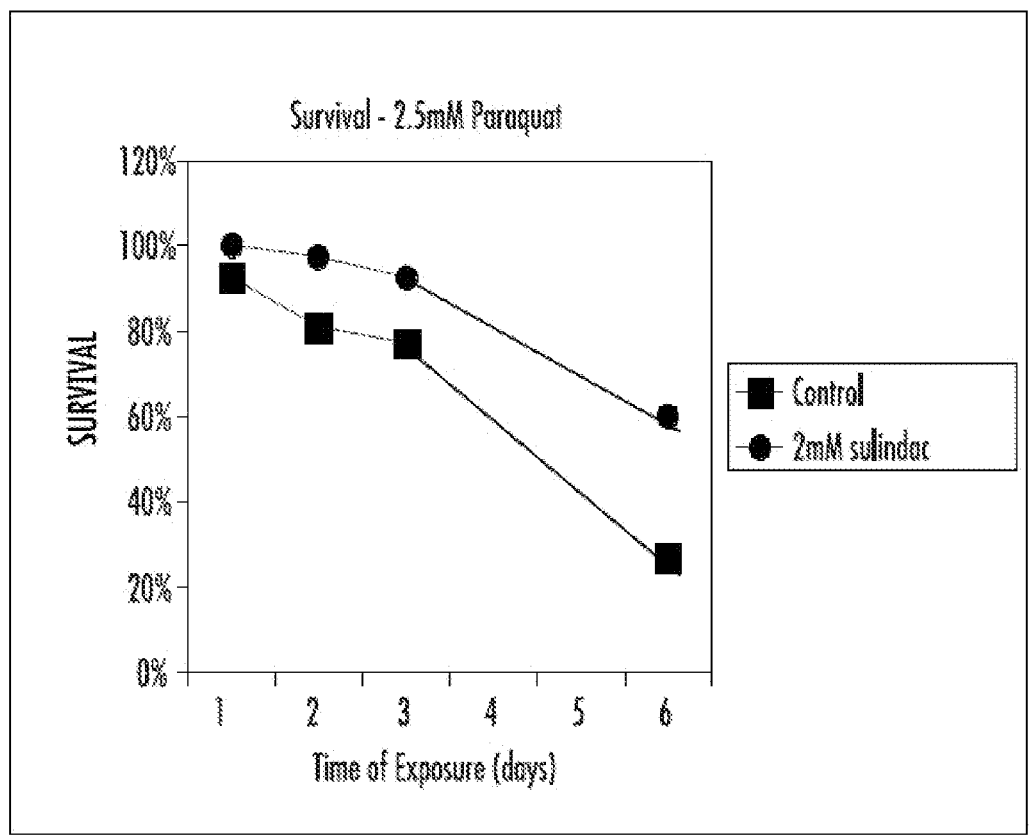
FIG. 10 is a graph showing enhanced survival of sulindac-treated flies exposed to oxidative stress induced by paraquat.

In the group treated with 2.5 mM paraquat, approximately 80% and 25% of the flies in the untreated control group, respectively, were alive after 3 and 6 days of paraquat exposure. By contrast, approximately 95% and 60%, respectively, of the flies treated with 2 mM sulindac remained alive at the 3 day and 6 day time points (FIG. 10). Similar results were observed in the groups exposed to higher concentrations of paraquat. For example, in groups exposed to 10 mM paraquat, the respective survival rates after 2 and 3 days were approximately 50% and 17% in the controls and 85% and 57% in the sulindac treated groups. These results demonstrate that administration of a methyl sulfoxide-containing compound that is a substrate for MsrA can lengthen the lifespan of paraquat-exposed flies. Earlier studies showed that over expressing MsrA enzyme in transgenic flies extended their lifespan. The present data provide evidence that increasing the intracellular level of a substrate for the Msr system can also provide a protective effect against damaging ROS species, leading to increased longevity under conditions of oxidative stress.

Example 8

Sulindac Promotes Cell Survival in Neuronal Cells Subjected to Oxidative Damage by MPP+

This example demonstrates a protective effect of sulindac on PC-12 cells following insult with MPP+, a toxic compound that selectively destroys dopaminergic neurons in vitro, and in an in vivo animal model of Parkinson's disease.

Materials and Methods.

MPP+ neurotoxin. The neurotoxin 1-methyl-4 phenyl-1,2,3,6-tetrahydropyridine (MPTP) when given to both humans and primates results in a clinical syndrome closely similar to Parkinson's disease. The compound is metabolized to 1-methyl-4-phenylpyridinium (MPP+) by monoamine oxidase B and is subsequently selectively taken up by dopaminergic terminals and concentrated in the neuronal mitochondria in the substantia nigra. MPP+ inhibits complex 1 of the electron transport chain and is thought to cause irreversible inactivation of the complex by generating free radicals (Hartley A., Stone J. M., Heron C, Cooper J. M., and Schapira A. H. V. *J. Neurosci.* 63: 1987-1990, 1994). MPP+ increases superoxide synthesis in vivo and in vitro. MPP+ damage is decreased in transgenic mice overexpressing superoxide dismutase, suggesting that free radicals are involved in its neurotoxicity.

Cell culture. PC-12 cells were initially grown overnight in Dulbecco's modified Eagle's medium containing high glucose (Gibco #11195-065), 5% fetal calf serum and 10% horse serum in 9 cm dishes. The cells were then transferred to 6 cm dishes and grown in the same medium without glucose but using sodium pyruvate (Gibco #11966-025) as the sole energy source. These cells were pretreated with sulindac (Sigma) at concentrations of 0.1, 0.2, or 0.5 mM for 48 hours, the medium containing the sulindac was removed and replaced with fresh medium The cells were then incubated for 24 hours in medium containing MPP+ at a final concentrations of 0.2 mM. Control cells were incubated in MPP+-free medium. At the end of the 24 hr period, cell viability was assayed by trypan blue exclusion.

Results.

Referring to Table 7, the results show that 0.2 mM MPP+ was highly toxic to PC-12 cells, causing approximately 85% of the cells to die (15% cell survival) following a 24 hour treatment with this compound. Pretreatment with sulindac prior to MPP+ insult was protective against cell death, exhibiting a dose-response with approximately 35% cell death (65% cell survival) following pretreatment with the maximum concentration tested, i.e., 0.5 mM. In the absence of MPP+, sulindac had no effect on the viability of the cells.

TABLE 7

Effect of Sulindac on the Viability of PC-12 Cells Treated with MPP+.

| Sulindac (mM) | Dead cells (%) Exp 1 | Dead cells (%) Exp 2 |
| --- | --- | --- |
| 0 | 85 | 87 |
| 0.1 | 67 | 74 |
| 0.2 | 55 | 39 |
| 0.5 | 34 | 35 |

Example 9

Sulindac Extends the Lifespan of a Transgenic Mouse Model of Familial Amyotrophic Lateral Sclerosis (ALS)

This example provides evidence that sulindac, a methyl sulfoxide containing compound that acts as a substrate for MsrA enzymes can significantly extend lifespan, increase motor neuron cell count and improve motor performance in a mouse model of ALS based on a mutation in superoxide dismutase (SOD1).

Materials and Methods:

ALS is an adult onset neurodegenerative disease of generally unknown etiology. ALS is most commonly sporadic, with about 10% of cases being inherited as an autosomal dominant familial form. It is now known that about 20% of the familial cases are associated with a mutant form of Cu/Zn SOD (Rosen, D. R., et. al., (1993) *Nature* 362:59-62). Although the protein harbors a mutation (over 100 different SOD mutations having been documented in ALS patients), it is still enzymatically active. Oxidative damage is one of the main hypotheses for the toxicity of the mutant protein. The animals used in this study express a mutant form of SOD that models a mutation described in patients with ALS.

Transgenic mice expressing a mutant form of SOD similar to that found in human ALS patients were used for this study. Transgenic male mice with a G93A human SOD1 (G1H/+) mutation (B6SJL-TgN (SOD1-G93A)1 Gur; Jackson Laboratories, ME) were used to breed with female B6SJL mice (Jackson Laboratories, ME). The F1 generations were genotyped for the G93A mutation with polymerase chain reaction (PCR) using tail DNA, and two specific primers from the SOD1 gene.

Sulindac administration. G93A mice were treated with sulindac at two different doses, i.e., 300 PPM and 450 PPM, which was mixed into their food beginning on postnatal day 30. Three groups were examined (i.e., 300 PPM, 450 PPM sulindac and controls). Motor performance was assessed by Rotarod testing for each group and survival time was recorded.

Motor function testing. Mice were trained for 2-3 days to become acquainted with the Rotarod apparatus (Columbus instruments, Columbus, Ohio). Rotarod performances were assessed in G93A mice starting at 60 days of age. The testing began with placing the mice on a rod that rotates at 12 rpms. The time period that the mice stayed on the rod before falling off was recorded as a measurement of the competence of their motor function. Three trials were performed, and the best result of the three trials was recorded representing the status of the motor performance. Mice were tested twice a week until they could no longer perform the task.

Survival times. The initial sign of disease in G93A transgenic mice is a resting tremor that progresses to gait impairment, asymmetrical or symmetrical paralysis of the hind limbs, and ultimately complete paralysis at the end stage.

Mice were sacrificed when they were unable to roll over within 20 seconds after being pushed on their side. This time point was determined to be the time of survival, at which time the mice were sacrificed.

Light microscopic immunocytochemistry. Mice were perfused transcardially with cold 0.1M phosphate-buffered saline (PBS) for 1 minute followed by cold 4% paraformaldehyde in PBS for 10 minutes. The spinal cords were removed rapidly, blocked coronally, and post-fixed in 4% paraformaldehyde in PBS for 6 hours. Blocks were cryoprotected in 30% sucrose for 24 hours and were sectioned on a cryostat at a thickness of 35 micrometers. All protocols were conducted within NIH guidelines for animal research and were approved by the Institutional Animal Care and Use Committee (IACUC).

Serial transverse sections (50 μm thick) were cut on a cryostat and collected for Nissl staining. Every fourth section was analyzed for neuronal volume and number using the optical fractionator and nucleator probes of the Stereo Investigator System (Microbrightfield, Colchester, Vt.). Six tissue sections of the lumbar spinal cord from each mouse were analyzed. All cells were counted from within the ventral horn below a horizontal line across the gray matter through the ventral border of the central canal. Photomicrographs were taken on a Zeiss Axiophot II microscope.

Statistical analysis. Statistical analysis of survival was performed using Kaplan-Meier test for survival measured in postnatal days, Fisher's Test for mean age of death analysis, and Scheffe test for motor performance.

Figure 11:
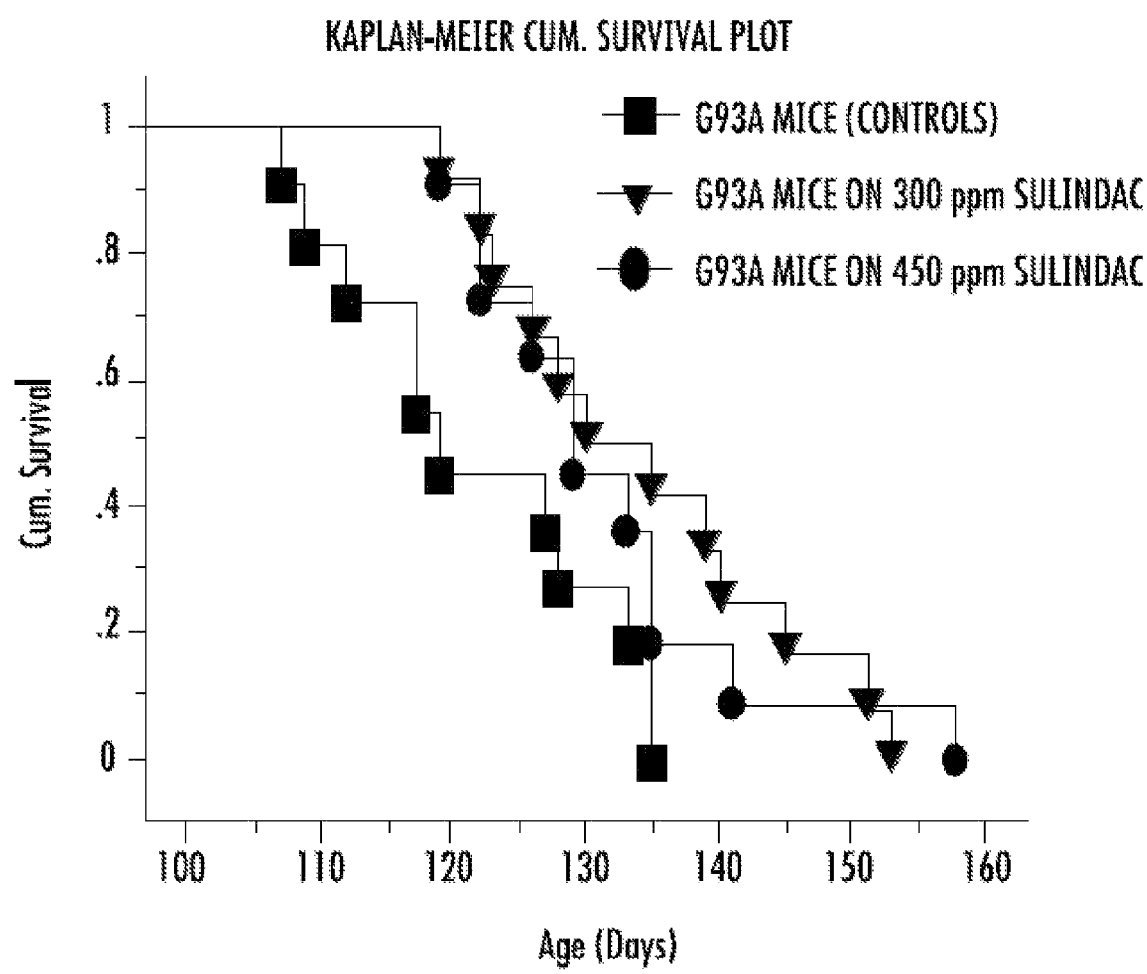
FIG. 11 is a graph showing enhanced survival of G93A transgenic mice over expressing a mutant superoxide dismutase with neurodegenerative disease treated with sulindac.

Results:

Referring to FIG. 11, G93A mice treated with 450 PPM sulindac survived an average of 131.17±10.9 days. This was a 7% increase over control mice, which survived an average of 123.16±11 days (P=0.083). G93A mice treated with 300 PPM sulindac also exhibited extended survival (a 10% increase) relative to the controls, with mean survival time of 135.17±11.4 days (P=0.02).

The results of several statistical tests of the data shown in FIG. 11 are presented in Table 8.

TABLE 8

Rank Test

| | Chi-Square | DF | P-Value |
|---|---|---|---|
| Logrank (Mantel-Cox) | 6.744 | 2 | .0343 |
| Breslow-Gehan-Wilcoxon | 7.796 | 2 | .0203 |
| Tarone-Ware | 7.374 | 2 | .0250 |
| Peto-Peto-Wilcoxon | 7.661 | 2 | .0217 |
| Harrington-Fleming (rho = .5) | 7.374 | 2 | .0250 |

Figure 12:
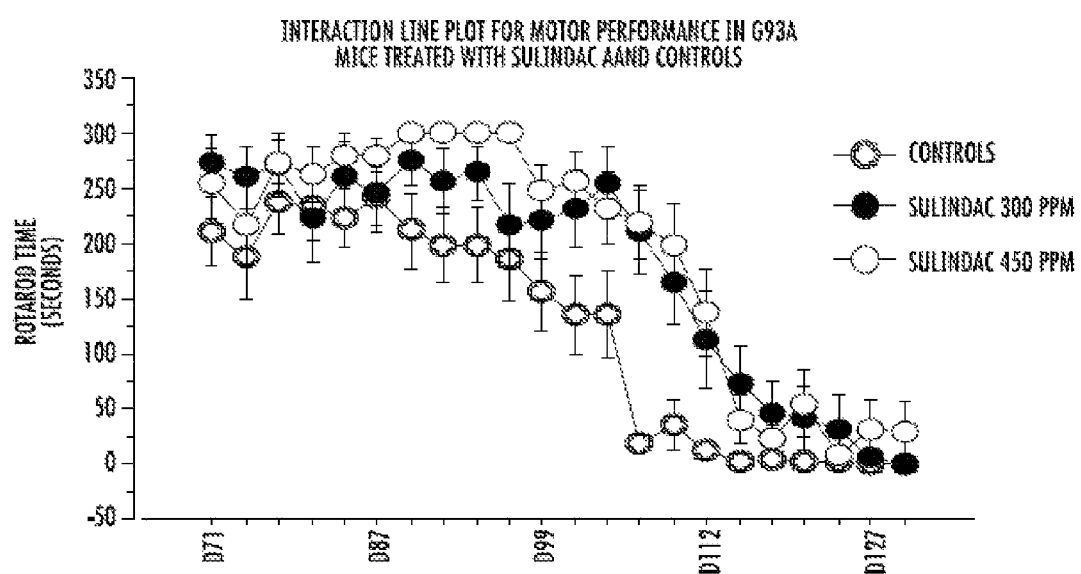
FIG. 12 is a graph showing enhanced motor performance of sulindac-treated transgenic G93A mice.
Figure 13:
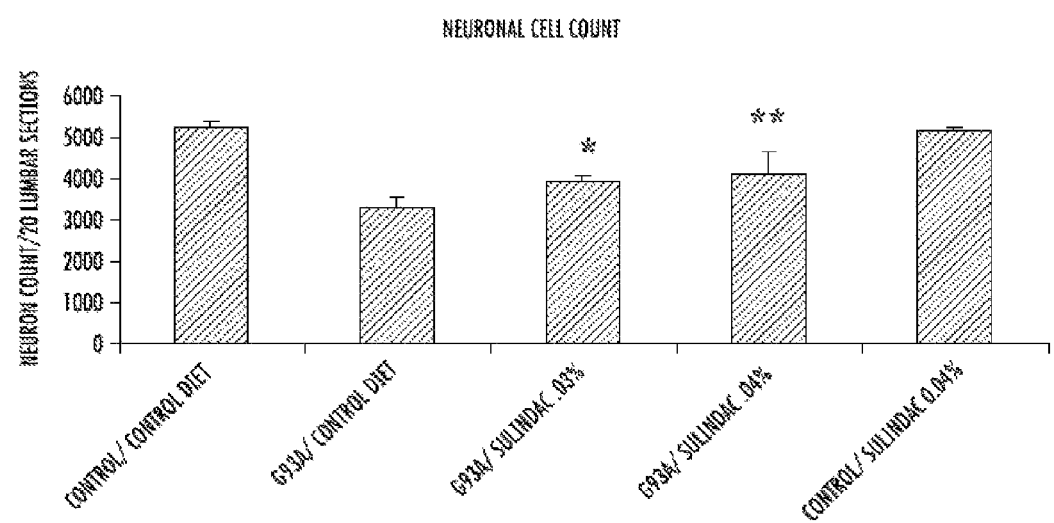
FIG. 13 is a graph showing neuronal cell counts in sections of spinal cords of G93A mice. Neuronal cell survival is significantly higher in animals receiving sulindac.

The sulindac-treated groups showed a significant improvement in motor performance, as evaluated by Rotarod performance times (FIG. 12). Microscopic analysis of spinal cord sections revealed that the sulindac-treated mice had significantly higher counts of motor neurons as compared with G93A controls (FIG. 13). Differences between the 300 PPM and 450 PPM sulindac groups were not significant (FIG. 13 and Table 9).

TABLE 9

Scheffe for Motor Performance

| | Mean Diff. | Crit. Diff. | P-Value | |
|---|---|---|---|---|
| Controls, Sulindac 300 PPM | −59.443 | 54.695 | .0308 | S |
| Controls, Sulindac 450 PPM | −73.119 | 53.271 | .0053 | S |

TABLE 9-continued

Scheffe for Motor Performance

| | Mean Diff. | Crit. Diff. | P-Value |
|---|---|---|---|
| Sulindac 300 PPM, Sulindac 450 PPM | −13.676 | 56.815 | .8267 |

Example 10

R- and S-Epimer Separation

Figure 15:
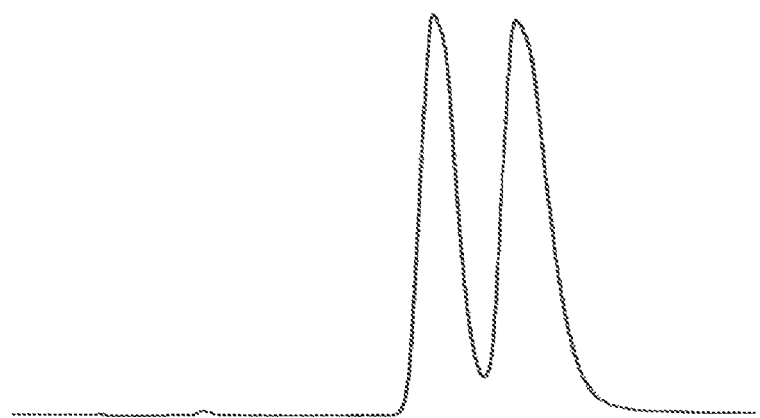
FIG. 15 is a chromatogram showing the separation of the R&S-epimers of sulindac using a chiral column. Sulindac (7 mg/ml) was dissolved in a mixture of hexane/ethanol (65/35) containing 0.1% acetic acid and 75 µl of this solution applied to the chiral column. The column was developed with the above solvent at a flow rate of 1.5 ml/min and 300 µl fractions collected. The elution of the sulindac was followed by monitoring the optical density at 256 nm. Two peaks are observed eluting after 22.5 and 28 minutes (OD 256). The R-form elutes first (22.5 min) followed by the S-form (28 min).

The R- and S-epimers of sulindac can be separated using chiral columns and HPLC. The sulindac epimers were separated and isolated from the racemic mixture with scale-up of sufficient quantities for our studies using a preparative chiral column. The chiral column (R,R)-Welk-01 chiral column (25 cm×4.6 mm) was purchased from Regis Technologies (Milton Grove, Ill.). As shown in FIG. 15, the 2 epimers of sulindac were separated quite well, under the conditions described in the legend of FIG. 15. Two peaks were observed eluting after 22.5 and 28 min. The peak tubes were combined and the solvent evaporated. The separated epimers were then dissolved in 1M Tris Cl pH 7.4. In order to determine which epimer was present in each peak, the material in each peak was incubated with *Escherichia coli* MsrA and 15 mM DTT, which would convert the S-epimer to sulindac sulfide. At the end of the incubation, the reduced product was extracted into benzene and the optical density read at 350 nm as previously described (Etienne F, Resnick L, Sagher D, Brot N, Weissbach H. Biochem Biophys Res Comm. 2003; 312:1005-10). It was determined that the peak eluting at 28 minutes was the S-epimer of sulindac.

Figure 16:
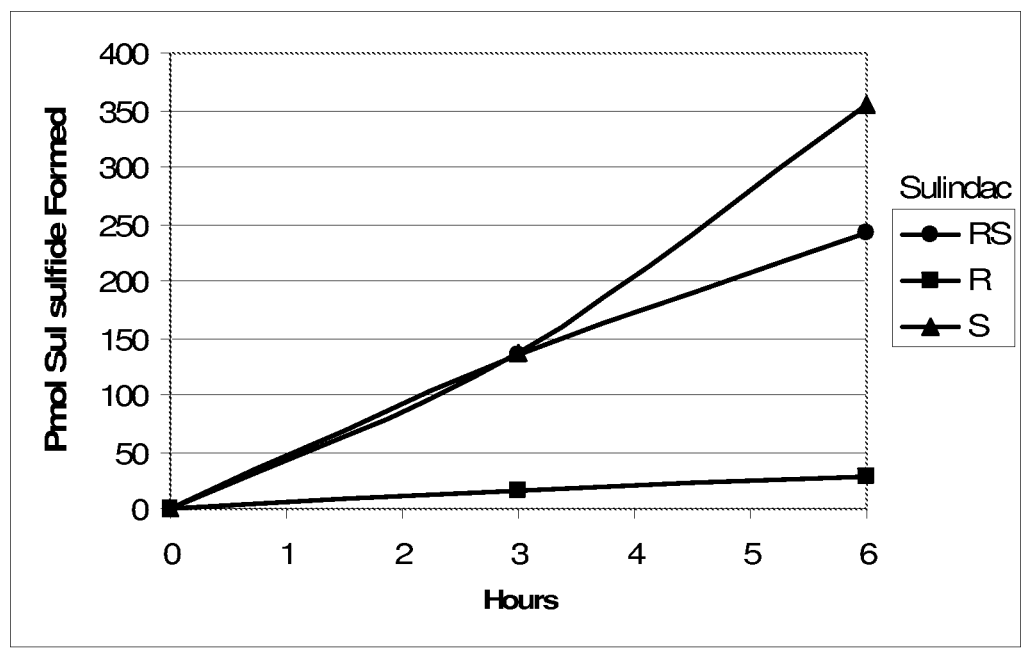
FIG. 16 is a graph showing the metabolic conversion of the R & S epimers of sulindac to the sulfide form in cardiac myocytes. The amount of sulindac sulfide formed by $10^6$ cells incubated with 400 µM sulindac, R,S or RS mixture is measured as a function of time of incubation. The assay was performed by HPLC separation of cell lysates, using a C18 column and a mobile phase of 50/50% 50 mM sodium acetate, pH 4.73, and acetonitrile. The absorbance was measured at 330 nm.

As shown in FIG. 16, in normal cardiac myocytes, the R-epimer of sulindac was very poorly converted to the sulfide (greater than 10-fold less conversion) compared to the S-epimer, under the conditions described in the legend.

Table 10, shows that two normal cell lines (lung and cardiomyocytes) do not reduce the R epimer as efficiently as the S epimer (<10% R/S). However, in 3 cancer cell lines (Lung, HeLa, and skin SCC), there is an enhanced conversion of the R-epimer (greater than 40%), unlike that found in normal cells (less than 10%). A significant reduction of the R-epimer of sulindac, although not seen in normal cells, has been observed in some malignant cells.

The cells are incubated with 200 μM R- or S-Sulindac epimer for 4 hours in a defined, serum-free medium (EX-CELL©). After incubation, the cells are collected, rinsed and lysed with acetonitrile. The cytosolic contents are separated on a C-18 column.

TABLE 10

| | Amount Formed (picomoles) | | |
|---|---|---|---|
| Cell | R-epimer | S-epimer | R/S (%) |
| Cancer | | | |
| Lung | 7.5 | 17.7 | 42 |
| HeLa | 9.3 | 7.9 | 118 |
| Skin | 35.3 | 57 | 62 |
| Normal | | | |
| Lung | 2.2 | 35 | 6 |
| Cardiomyocyte | 11.6 | 120.9 | 9 |

Example 11

Prevention and Treatment of Cancer

Normal lung cells were treated with 500 µM sulindac-(R+S; near 50% each), 500 µM sulindac-R (>99% R; <1% S) or 500 µM sulindac-S (>99% S; <1% R) for 48 hr. The sulindac-R and sulindac-S samples were obtained from a racemic mixture of epimers using a chiral column analogous to the process described above. The cells were washed and then exposed to the indicated concentration of tert-Butyl Hydroperoxide (TBHP) for 2 hr. Cell viability was measured using the standard MTS assay. A background absorbance of 0.12 was subtracted from average of four replicate samples. The data are plotted as a bar graph because the concentrations are not in equal intervals. The error bars are the SEM of four replicate samples. The data are presented on three separate graphs using the untreated samples from that plate.

Figure 17:
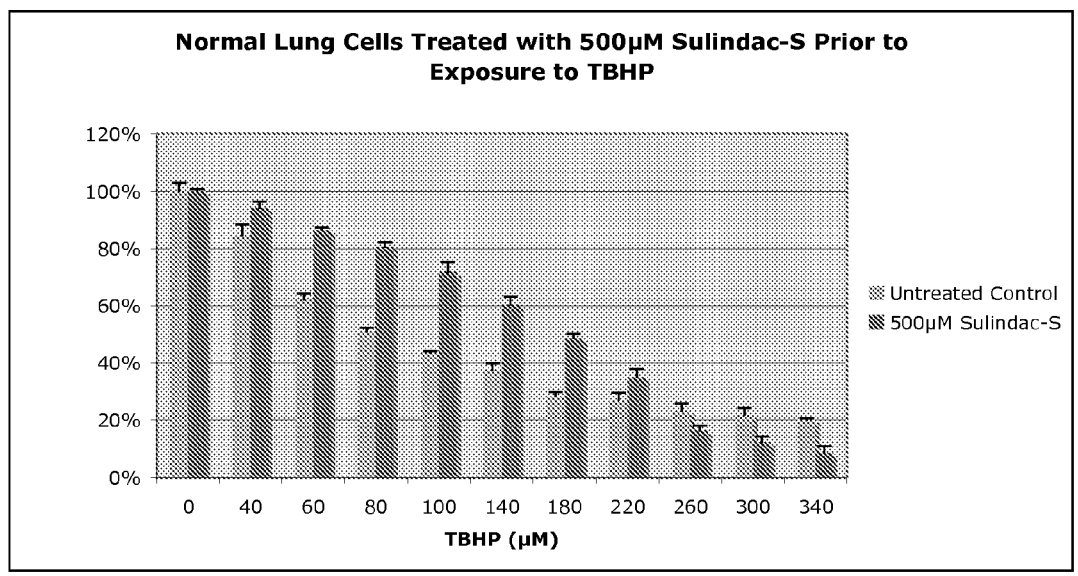
FIG. 17 is a graph showing the viability of normal lung cells treated with 500 µM sulindac-S (S-epimer of sulindac) prior to exposure to tert-butyl hydroperoxide (TBHP).
Figure 18:
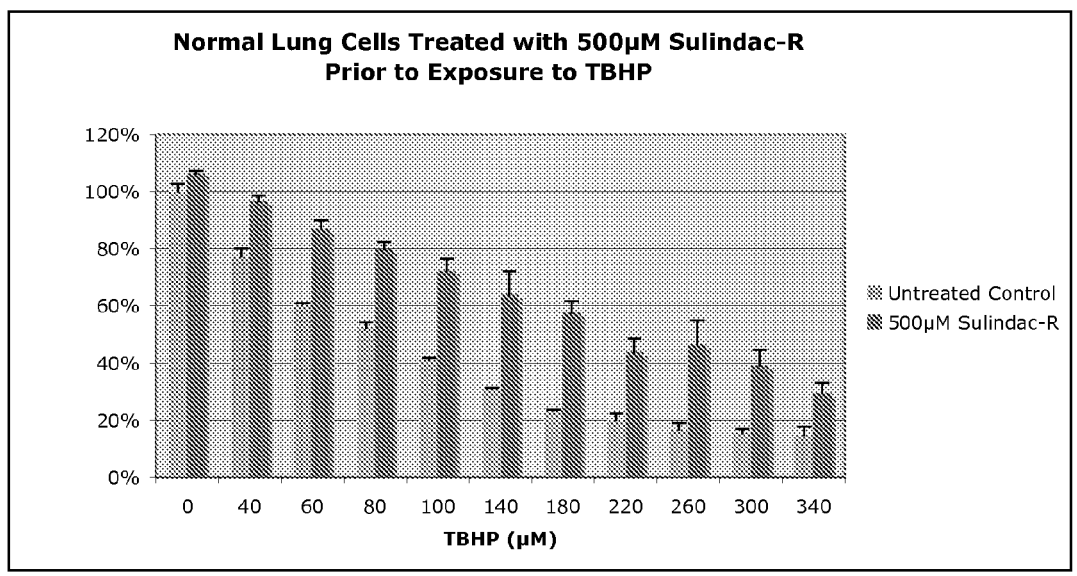
FIG. 18 is a graph showing the viability of normal lung cells treated with 500 µM sulindac-R (R-epimer of sulindac) prior to exposure to tert-butyl hydroperoxide (TBHP).

The results show that sulindac-R not only provides protection, it protects better as compared to sulindac-(R+S) or Sulindac-S. The results for sulindac-(R+S) are similar to previous experiments performed by the present inventors where the protection declined rapidly after ~80-100 µM TBHP. Sulindac-S provided protection to ~180 µM TBHP concentration with the error bars beginning to overlap at ~220 µM TBHP. (See, FIG. 17). For sulindac-R, there is evidence of protection as high as 340 µM TBHP (see FIG. 18).

Figure 19:
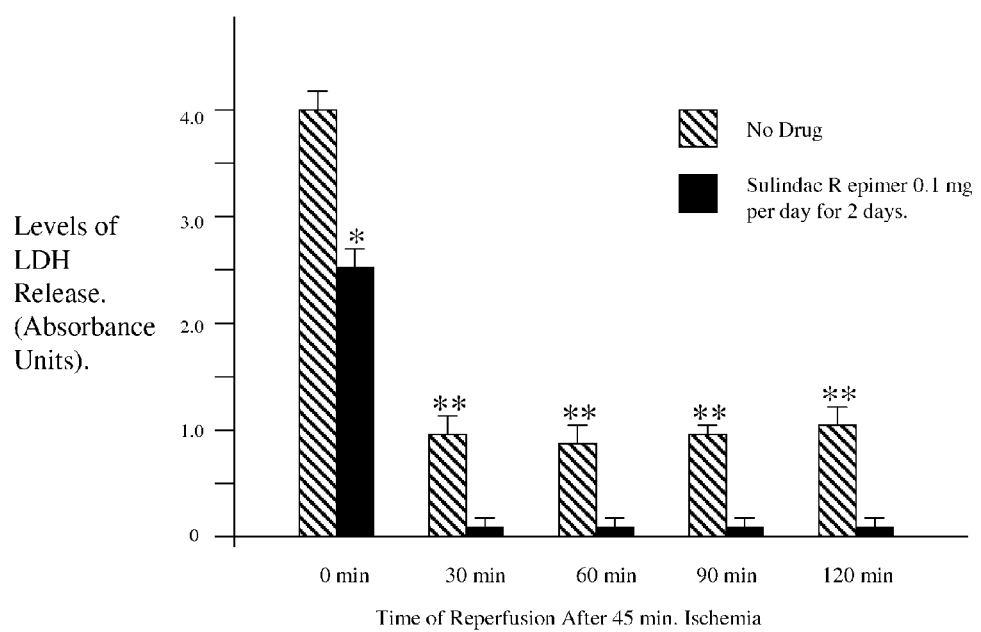
FIG. 19 is a graph showing in vivo administration of sulindac-R epimer decreases LDH release following ischemia/reperfusion in Langendorff heart.

As shown in FIG. 19 the feeding of the R epimer of sulindac to rats protects their hearts from oxidative damage due to ischemia and reperfusion. In these experiments the rats received 0.1 mg of the R epimer of sulindac in their diet for 2 days. The hearts were removed, exposed to ischemia for 45 minutes and then perfused for 2 hours (reperfusion) using a Langendorff procedure. The cellular damage was measured by assaying for the release of lactic dehydrogenase (LDH).

Other Embodiments

This description has been by way of example of how the compositions and methods of the invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A method of protecting an organ from damage caused by reperfusion injury in a subject who will experience an ischemic event in the organ, the method comprising administering to subject a pharmaceutical composition comprising sulindac and a pharmaceutically acceptable carrier.

2. The method of claim 1, wherein the pharmaceutical composition is formulated for sustained release.

* * * * *